United States Patent [19]

Michl et al.

[11] Patent Number: 5,405,550
[45] Date of Patent: Apr. 11, 1995

[54] COMPOUNDS AND METHODS BASED ON [1.1.1]PROPELLANE

[75] Inventors: Josef Michl, 501 Aurora Ave., Boulder, Colo. 80302; Piotr Kaszynski; Andrienne C. Friedli, both of Pasadena, Calif.

[73] Assignee: Josef Michl, Boulder, Colo.

[21] Appl. No.: 927,228

[22] Filed: Aug. 10, 1992

Related U.S. Application Data

[63] Continuation of Ser. No. 671,174, Mar. 15, 1991, abandoned, which is a continuation of Ser. No. 202,272, Jun. 3, 1988, abandoned.

[51] Int. Cl.$^6$ ............... C07C 255/00; C07C 13/36; C09K 19/52
[52] U.S. Cl. .................. 252/299.01; 558/432; 560/129; 560/147; 560/152; 568/379; 570/130; 570/187; 570/188; 585/23; 252/299.63
[58] Field of Search ........... 252/299.01, 299.6, 299.63; 558/429, 432; 560/124, 129, 147, 152; 568/303, 379; 570/130, 187, 188; 585/23

[56] References Cited

PUBLICATIONS

Schluter, (1988) Macromolecules 1988, 21, No. 5 at pp. 1208–1211.
Bunz, et al., "Bridgehead–coupled bicyclo[1.1.1]pentanes: synthesis and structure", Chemical Abstracts, vol. 109, No. 230356u (1988).
Patrick, et al, "Replacement of the carboxylic acid function with fluorine", Can. J. Chem., vol. 64, pp. 138–141 (1986).
Wiberg, et al., "[1.1.1]Propellane: Reaction With Free Radicals", Tetrahedron Letters, vol. 27, No. 14, pp. 1553–1556 (1986).
Belzner, et al., "Tetracyclo[5.1.0.0$^{1,6}$.0$^{2,7}$]Octane: Some Unexpected Addition Reactions and a New Synthesis", Tetrahedron Letters, vol. 28, No. 27, pp. 3099–3102 (1987).
Bunz, et al Chem. Ber. 121, 1785, 1988.
Raszynski et al J. Am. Chem. Soc. 110, 5225, 1988.
Applequist et al J. Org. Chem. 47, 4985, 1982.
Bunz et al Manuscript: Synthesis and Structure . . . .

*Primary Examiner*—Shean Wu
*Attorney, Agent, or Firm*—Greenlee and Winner

[57] ABSTRACT

Molecular bulding beams, liquid crystals, and surfactants in the form of compounds based on [1.1.1]propellane, including poly[1.1.1]propellanes. Molecular building beams having a telomeric or polymeric chain staff, and linking groups functionalized on one or both ends of the staff. A system for linking the beams to connecting units to construct molecular structures of various forms, such as whips, combs, scaffoldings, nets, or stars. Other broad aspects of the invention provide liquid crystals and surfactants. The liquid crystals include telomeric or polymeric compounds functionalized with flexible end groups, while the surfactant compounds are functionalized with surface active end groups. Methods of synthesizing the various compounds ar also provided.

39 Claims, 5 Drawing Sheets

COMPOUNDS AND METHODS BASED ON [1.1.1]PROPELLANE

This application is a continuation of U.S. patent application Ser. No. 07/671,174, filed Mar. 15, 1991, now abandoned which is incorporated in its entirety by reference herein U.S. patent application Ser. No. 07/671,174 is in turn a continuation of U.S. patent Ser. No. 07/202,272, filed Jun. 3, 1988, now abandoned.

BACKGROUND

The government may own certain rights in the present invention pursuant to NSF Contract No. CHE 8796257.

This invention relates to a series of telomers, polymers and copolymers of the monomer, [1.1.1]propellane, their manufacture, their use, and their manufacture for various applications.

These compounds have unprecedented structures. Due to the presence of bicyclo[1.1.1]pentane rings, they contain up to 14 kcal/mol strain energy per carbon atom. The rigid-rod nature of poly[1.1.1]propellane segments and their tendency to crystallize provide interesting properties.

[1.1.1]propellane is a hydrocarbon compound having the following structure:

(1)

This compound will be referred to at various places herein as "(1)" referring to the reference number shown below the structure. Other compounds will be similarly referenced.

Because of the highly strained configuration of this compound at the two bridgehead carbons, [1.1.1]propellane has received much attention in recent years.

Carbon atoms normally have a tetrahedral geometry represented by the following:

However, the two bridgehead carbons of [1.1.1]propellane have their geometry inverted such that all four bonds lie on one side of a plane. Thus, the bridgehead carbons of [1.1.1]propellane have the following geometry:

As a result of the inverted geometry, [1.1.1]propellane has a very high strain energy.

The first preparation of (1) known to Applicants was described by Wiberg and Walker, 104 J. Am. Chem. Soc. at pp. 5239-5240 (1982), via a reaction of 1,3 dibromobicyclo[1.1.1]pentane with tert-butyllithium in pentane ether. Preparation by this procedure is relatively laborious and yield is low. The article also reports on various properties of (1), and shows reactions of (1) to give 3-methylenecyclobutyl acetate and 3-methylenecyclobutene.

A two step preparation of [1.1.1]propellane from commercially available materials was described by Semmler et al., 107 J. Am. Chem. Soc. at pp. 6410-6411 (1985). The first step involved preparation of 1,1-bis(-chloromethyl)-2,2-dibromocyclopropane, and the second step reacted this compound to produce a solution of (1) in pentans/ether. The article also reports on reaction of (1) to a thioether, preserving the bicyclo[1.1.1]pentane ring structure.

Free radical addition to (1) is discussed in Wiberg et al., 27 Tetrahedron Letters, No. 14 at pp. 1553-1556 (1986). It is reported that reaction of (1) with cyanogenbromide gave the 2:1 adduct as the major product, which a significant amount of 3:1 adduct. It is stated that a small amount of 2:1 adduct was observed in the addition of chloroform and carbon tetrachloride to (1).

Applicants have improved the two-step procedure for the preparation of (1), and have also developed a new procedure, wherein e.g. a 5-20 g amount of [1.1.1]propellane at a time can be prepared conveniently. The inventors believe that further scale-up is possible. This development makes this highly unusual compound available as a synthetic starting material.

Applicants' novel synthesis of [1.1.1]propellane in a pentans solution (see Examples 6 and 12 below) provides the advantage of avoiding subjecting the [1.1.1]propellane to the presence of ether. Quite often, when (1) is desired to be used as a starting material to synthesize various compounds in accordance with the present invention, the presence of ether is undesired. For example, reaction of HCOOMe with (1) in the presence of ether produces diethyl ether adducts as the major products, with the desired methyl [n]staffanecarboxylate (see (2d) below) as only a minor product. In contrast, reaction of HCOOMe with [1.1.1]propellane in pentane produces only (2d). As another example, production from (1) of a [2]staffane functionalized at both ends with iodine can not be achieved in the presence of ether. Applicants' method thus provides a [1.1.1]propellane solution free of ether, thereby overcoming the disadvantages experienced by the literature synthesis.

Applicants have also effected radical addition of various reagents across the bridgehead-bridgehead bond in [1.1.1]propellane, leading to several functionalized 1,3-disubstituted bicyclo[1.1.1]pentanes.

In view of the reactivity of [1.1.1]propellane towards radicals, it tends to undergo radical-induced polymerization. Moreover, since an efficient route from (1) to bicyclo[1.1.1]pentane-1,3-dicarboxylic acid has resulted from investigation by the inventors of radical additions to (1) as well, this long-known yet previously poorly accessible diacid is now available via the present invention in large quantities for the synthesis of additional polymers by condensation.

SUMMARY OF THE INVENTION

1. Molecular "Tinkertoy" Construction System

The first broad aspect of the present invention provides a molecular "Tinkertoy" building system, wherein various molecular civil-engineering structures can be constructed. The structures are generally constructed by attaching molecular building beams as described below to connecting units.

Thus, in accordance with one embodiment of the present invention, a molecular building beam is provided comprising a poly[1.1.1]propellane having the following formula:

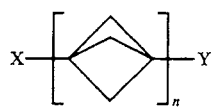

(2)

wherein n is the chain length, and X and Y are linking groups.

The term "poly[1.1.1]propellane" is used to mean a molecule having a plurality of bicyclo[1.1.1]pentane rings (shown in brackets above) linked together as shown in formula (2). The term includes both telomers or oligomers (i. e. n≦about 10) and polymers (i. e. n>about 10).

The term "linking group" means a group attached to the end of a polymer or telomar which has the ability to join the polymer or telomar to which it is attached as a ligand to connecting units, such as metal atoms.

Nanotechnology, i.e. custom design and construction of molecular-size mechanical structures, has been a subject of speculation for some time. The present invention provides for the use of telomerized and polymerized [1.1.1]propellanes as molecular building beams, the beams perferably being end-functionalized inert, insulating, transparent and straight and having a van der Waals radius of 2.3 A and a length increment of 3.35 A for use as construction elements. The term "[n]staffanes" is used herein to mean the parent hydrocarbons, where n is the chain length. Singly functionalized telomers (2), may be prepared by a one-step synthesis. Doubly end-functionalized telomers of [1.1.1]propellane may also be prepared by a one-step synthesis.

Previously described molecules of this type were the formal telomers of [2.2.2]propellane (17), known up to n=2, and used as spacers in studies of energy and election transfer.

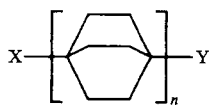

(17)

Unlike the synthesis of (2), preparation of the higher members of this series is laborious.

In a preferred embodiment of the present invention, the poly[1.1.1]propellane is a telomer, wherein n is 2, 3, 4, or 5.

Numerous possibilities are available for the linking groups X and Y in formula (2). It should also be appreciated that either X or Y could by hydrogen, wherein the beam comprises a singly end-substituted poly[1.1.1]propellane. In this case, only the substituted end will be involved in linking with a connecting unit.

The linking groups X and Y may be selected according to the desired geometry or strength of the molecular structure to be built. It is believed that carbon-carbon linking between the linking group and staff provides a stronger bond than a heteroatom linking. Thus, X may be a group which includes a heteroatom (i.e. an atom other than carbon), the heteroatom bing bonded to a bridgehead carbon atom of the staff. If a stronger bond is desired, X may be a group which includes a carbon atom, the carbon atom being bonded to a bridgehead carbon atom.

The beams may be attached to the connecting units at various angles in accordance with the geometry of the linking group on the beams. Thus, if a 180° linking is desired, such linking groups as —CN, —NC, $C(CH_2O)_3P$, $C(CH_2CH_2)N$, $CH(COCH_3)_2$, COOH, CSSH, or $C(CH_2SH)_3$ may be used. If a stronger linear bond is desired, then 1,4-phenylene could be selected.

Conversely, angular attachments can be provided by selecting e.g. —SR, —$PR_2$, —$NR_2$, —OR, —$BRr_2$, or —$SiR_2Cl$ linking groups, where R is perferably hydrogen or a parent or substituted alkyl or aryl. Stronger angular attachments may be obtained by using, e.g., a parent or substituted methyl, 1,3-phenylene, cis- or trans-ethylene, or quinone as a linking group.

In accordance with another embodiment, linking group X is a polymerizable linking group, for example, an alkene or substituted alkene. Thus, X could be vinyl, —$C_3H_5$, —$CH_2OC_2H_3$, —$COOC_3H_5$, etc. This embodiment provides for the construction of comb-like structures. That is, the unsaturated bonds in the linking groups can be polymerized, and the poly[1.1.1]propellane beams become "teeth" members extending from the polymer structure formed by the linking groups.

Another embodiment of the present invention provides a molecular building beam comprising a plurality of staffs, two ends, and a linking group connected to each end. The term "staff" is used to mean a single bicyclo[1.1.1]pentane ring or a plurality of directly linked bicyclo[1.1.1]pentane rings. The staffs are connected by connecting fragments. The connecting fragments may be conductive (e.g. alkynes), or may be magnetic (e.g. a group containing a metal having magnetic properties, such as Fe, Co, or Ni).

In a preferred embodiment, the connecting fragments are conductive, i.e. allowing the transfer of electrons. This embodiment provides the advantage of facilitating the transfer of electrons between the terminal linking groups of the staff. It is believed that such beams can have application to information transfer and storage technology.

Pure poly[1.1.1]propellane is an insulating chain since the bicyclo[1.1.1]pentane rings do not allow easy electron transfer therethrough. However, by inserting conductive fragments at various selected or random positions between the rings, electron transfer can be improved. The more the conductive fragments are added, the more rapid the electron transfer through the beam will become. Thus, the degree of conductivity can be selected by constructing beams with selected numbers of conductive fragments. Suitable conductive fragments include, for example, parent and substituted alkynes, alkenes, phenylenes, and quinones.

Thus, for example, using trans-ethylene as a connecting fragment, the following beam could be synthesized:

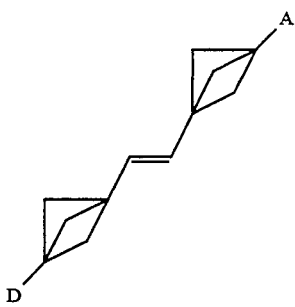

(4)

where A is a linking group having electron-accepting properties, and D is a linking group having electron-donating properties. It is believed that electrons can be transferred from D to A. Furthermore, by converting the trans-ethylene compound to the corresponding cis-ethylene compound, the inventors speculate that electron transfer between D and A might be further facilitated, since D and A would then be located more proximately to each other. Thus:

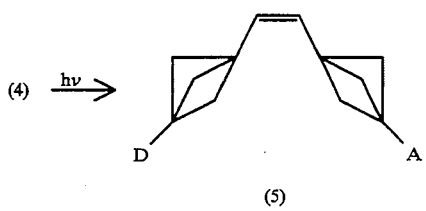

(4) $\xrightarrow{h\nu}$ (A)

(5)

In accordance with another embodiment of the present invention, a molecular structure ks provided, comprising a plurality of molecular building beams and a plurality of connecting units. Each beam comprises a poly[1.1.1]propellane having the formula as shown in (2) above. Each connecting unit has a plurality of accepting sites. At least one linking group of each beam is connected to an accepting site, thus joining the beams together.

Tne term "connecting unit" is used to mean a compound capable of joining one or more ligands. The term "accepting site" means a site on such connecting unit which binds a ligand to the connecting unit.

In one preferred embodiment, the connecting units are metals, such as metal atoms or groups of atoms or metal compounds. Most preferably, the metal is a transition metal, such as, for example, $Cu^{++}$ or $Rh_2^{++}$.

A plurality of the beams may be anchored to a supporting surface, such as a metal, crystalline, or glass surface. In this embodiment a layer of poly[1.1.1]propellane of desired thickness may be coated on the supporting surface.

The connecting units may be selected to determine the geometry of the structure. If the connecting units selected each have two accepting sites, then a whip structure may be created. If the connecting units are formed by polymerization of the linking groups themselves, a comb structure is created, wherein the molecular beams form the "teeth" of the comb. If the connecting units have three or more accepting sites, then starlike structures and net structures can be created.

In one preferred embodiment, the connecting units have at least six accepting sites. Four beams can be attached lying in a single plane and oriented 90° in relation to one another. In this way, a net structure is created. Two beams may also be attached to each connecting unit in perpendicular orientation to the plane of the other four attached beams. By this process, a scaffolding structure may be constructed.

Another aspect of the present invention provides a method for building molecular structures, comprising the steps of providing a plurality of molecular building beams and connecting units as described, and connecting the beams with the connecting units such that at least one linking group of each beam connects to an accepting site.

In one embodiment, the molecular beams are provided in a first solution (e.g., a benzene solvent), and the connecting units are provided in a second solution. The solutions are then mixed to provide the product.

In another embodiment, the molecular building beams are provided in a gaseous form by subliming the molecular beams from a solid source under vacuum. The connecting units may be provided on a solid surface, such as a metal or crystalline surface. The gaseous beams may then be directed onto the solid surface to connect the beams to the surface, e.g. by epitaxial growth.

For example, beams having a SiCl linking group may be dissolved in a benzene solution. The solution may then be contacted with a glass surface having OH contacting units. The SiCl and OH would react to give an SiO bond anchoring the bean to the glass surface, and HCl would go into solution.

Preferably, a plurality of bridge carbon atoms in the bicyclo[1.1.1]pentane rings are substituted. For example, carbons may be chlorinated or fluorinated. Chlorine substituents may subsequently be converted to other substituents if desired (e.g. an alkyl or aryl substituent). This provides the advantage of making the telomers or polymers more soluble.

2. Liquid Crystals

In accordance with another broad aspect of the present invention, a liquid crystal is provided comprising a plurality of molecules having the formula:

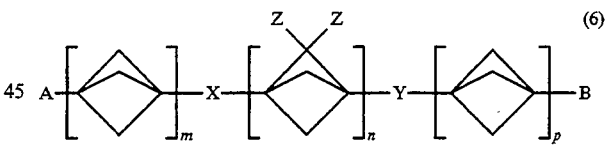

(6)

Where A and B are mesogenity supporting end groups, X and Y are mesogenity supporting connecting groups, Z is hydrogen or a substituent, and m, n, and p are chain lengths such that $m+n+p \geq 1$.

The term "mesogenity supporting" in connection with A, B, X, and Y means groups which cause the molecule in which they are included to display liquid crystalline properties. Generally, the molecule should be relatively long and flexible, and the mesogenity supporting groups should be able to maintain the molecule in a generally linear and floppy orientation.

A and B may be polar or nonpolar. Preferably, A and B are selected from cyano, nitro, carboalkoxys, acyls, and parent and substituted alkyls, alkoxyls, cycloalkyls, polycycloalkyls, and aryls. Preferably, A may be polar and B nonpolar.

Preferably, X and Y are selected from sulfur containing groups, oxygen contianing groups (e.g. oxygen, ester groups, $CH_2O$), a direct bond, ethane, ethylene, or acetylene.

These liquid crystals are believed to provide advantages over existing liquid crystals, displaying a lower viscosity. This provides a quicker response time for the liquid crystal, which may be important for industrial applications. Furthermore, the poly[1.1.1]propellane units are UV transparent, and thus photochemically stable. This should provide a long working life for the liquid crystals.

Preferably, A and B do not have an amine, sulfur, or hydroxyl group, since the presence of such a group generally makes the intermediate 1,3-disubstituted bicyclo[1.1.1]pentane compound B($C_5H_6$) I unstable.

In a preferred embodiment, a plurality of bridge carbons of the poly[1.1.1]propellane are substituted, for example with chlorine, fluorine, or cyano group. The substituted bridge carbons may be singly or doubly substituted. This changes the dielectric properties of the molecule, giving liquid crystals with negative dielectric anisotropy.

3. Surfactants

In accordance with another embodiment of the present invention, a surfactant is provided comprising a plurality of poly[1.1.1]propellane molecules having the formula shown in (2), wherein X is a functional end group and Y is a surface active group. X may be hydrogen such that the poly[1.1.1]propellane is singly end functionalized.

Suitable surface active groups may be selected from the range of known surface active groups. Preferably, Y is selected from $CO_2H$, $NH_2$, $P(O)(OH)_2$, $SO_3H$, end their salts. A plurality of bridge carbon atoms may be substituted, (e.g. chlorinated or fluorinated), which may increase the surface activity of the surfactant.

Methods for making the molecular building beams, liquid crystals, and surfactants are also provided by the present invention. These methods generally include the steps of providing a [1.1.1]propellane and reacting the [1.1.1]propellane with a polymerizing agent so that the [1.1.1]propellane polymerizes to a poly[1.1.1]propellane having an end group comprising a portion of the polymerizing agent. The end group may be converted to a linking group to provide a molecular building beam. Alternatively, the end group may be converted to a mesogenity supporting group to provide a liquid crystal. In a further alternative, the end group may be convened to a surface active group to provide a surfactant.

The term "polymerizing agent" is used to mean a compound which induces polymerization. The term "polymerization" is meant to include production of polymers of telomers. The polymerizing agent used above may be a radical polymerizing agent, whereby the polymerization proceeds along a radically induced mechanism. Alternatively, the polymerizing agent may be an anionic polymerizing agent, whereby anionic polymerization is induced.

Another embodiment of present invention provides a method for preparing an ether free [1.1.1]propellane, comprising the steps of providing a first solution including 1,1-bis(chloromethyl)-2,2-dibromocyclopropane, a cosolvent capable of complexing lithium, and an alkane; providing an alkyllithium solution and mixing the alkyllithium solution and the first solution to produce a second solution; and separating the third solution from the second solution, the third solution including [1.1.1]propellane and the alkane. All of the steps are performed in an inert gas, atmosphere, preferably argon or nitrogen.

Preferably, the cosolvent is N,N,N',N'-tetramethylethylenediamine (TMEDA). Another suitable cosolvent which is capable of complexing lithium is 1,4-di(exothy)butane.

Preferably, the alkane is pentane. The alkyllithium solution preferably comprises the alkyllithium dissolved in pentane. The alkyllithium is preferably butyllithium.

DETAILED DESCRIPTION OF THE INVENTION

Figure 1:
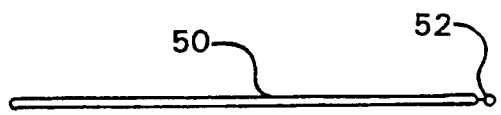
FIG. 1 is a diagrammatic illustration of a poly[1.1.1]propellane polymer which is singly end functionalized with a short end group.

The bicyclic cage string structure of poly[1.1.1]propellanes has two unique features that made it a potential source of several new classes of unusual polymers.

(i) Strain. The cage is a highly strained structure (the strain energy of bicyclo[1.1.1]pentane is 68 kcal/mol). Its destruction is believed to be strongly exothermic, giving it an autocatalytic character. In spite of this, many bicyclo[1.1.1]pentanes are remarkably stable up to quite high temperatures (e.g. 250°–300° C.). By incorporating the cage as a part of a polymer backbone, the polymer is believed to be quite stable until subjected to thermal or possibly radiation treatment at which point a deep-seated exothermic transformation occurs which leads to chain breaking. This property is potentially very useful in industrial applications, from the development of positive resists in the semiconductor industry to its use as a non-polarvulcanization agent.

(ii) Rod-like shape. The 1,3-linked ring system of bicyclo[1.1.1]pentane formed upon polymerization produces a rigid rod-like structure characteristic of cyclolinear polymers. Many polymers of this type have various industrially valuable properties, be it as homopolymers or as segments of copolymers. Rigid rod like materials with polar substituents find uses in the fields of piezoelectricity and liquid crystals. In addition, the rigid rod-like polymers or polymer segments can serve as models for many theoretical studies, prized by theoretical chemists and physicists.

Initial experiments by the inventors showed that [1.1.1]propellane can be induced to undergo radical polymerization. The polymer samples initially obtained were insoluble in all solvents that were tried and were quite intractable. They had high melting points, e.g. 270°–300° C., and once melted, decomposed rapidly with gas evolution, resulting in a weight loss of 80–90% and formation of a dark carbonaceous residue. X-ray diffraction revealed a high degree of crystallinity. Magic-angle spinning $^{13}C$ NMR analysis showed that the bicyclo[1.1.1]pentane structure was preserved in the polymer, and thus confirmed the poly[1.1.1]propellane structure.

It is believed that chain transfer plays an important role in the polymerization process, and many low-molecular weight telomers or oligomers with up to five bicyclo[1.1.1]pentane units have been isolated pure and characterized. These are thermally stable materials with quite high melting points and characteristic spectra. The mechanism assumed to be responsible for their formation can be exemplified on the case of the addition of methyl formate:

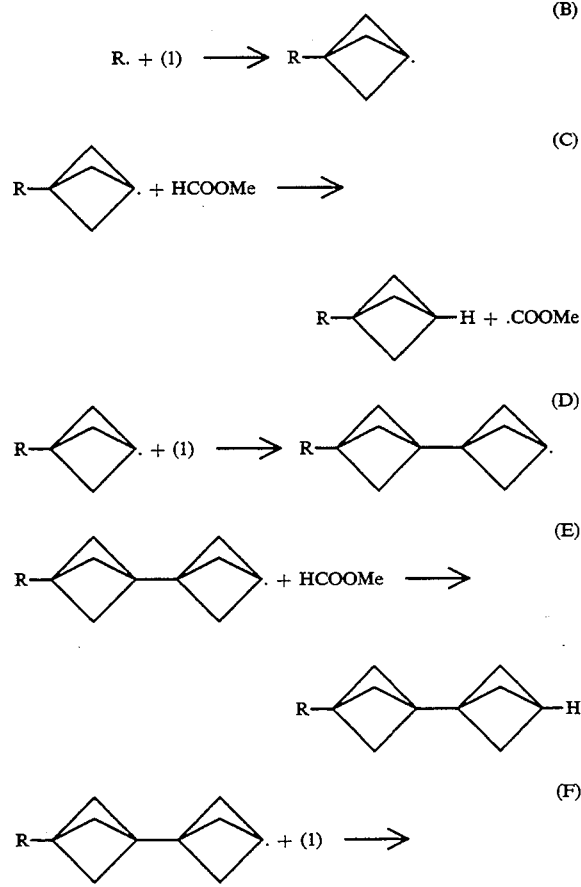

etc.

The formation of singly functionalized oligomers with the various end groups including the following has been observed by the inventors: COOMe, CH(COOEt)$_2$, C(COOEt)$_3$, CH(CN)$_2$, C(Me) (COOEt)$_2$, C(Ph) (COOEt)$_2$, CH(COMe)COOMe, CH(CN)COOMe, P(O)(OEt)$_2$. In addition, doubly functionalized oligomers have also been prepared, e.g. compounds with —SCOCH$_3$ groups at each end, some of which are liquid crystals.

X-ray structure determinations by the inventors on several of the oligomers have confirmed the straight-rod geometry. The inter-ring C—C bond appears to be quite short (e.g. 1.42–1.48 A) and intra-ring bridgehead—bridgehead separation appears to be about 1.9 A.

The radical addition reactions on [1.1.1]propellane have produced a series of 1,3-derivatives of bicyclo[1.1.1]pentane in addition to those already described in the literature. For example, an efficient procedure for the synthesis of 1,3-bicyclo[1.1.1]pentanedicarboxylic acid, shown below as (7b), is provided by the present invention, so that this promising starting material is now readily available for polycondensation and other reactions.

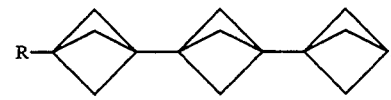

(7)

|     | X     | Y     |
|-----|-------|-------|
| (a) | H     | H     |
| (b) | COOH  | COOH  |
| (c) | Br    | Br    |
| (d) | COMe  | COMe  |
| (e) | R     | I     |
| (f) | R     | COMe  |
| (g) | R     | COOH  |
| (h) | R     | OH    |
| (i) | OH    | OH    |
| (j) | COOMe | COCl  |
| (k) | SH    | SH    |

Reference will be made at various places herein to compounds of this group by the reference number and letter listed above. Thus, for example, "(7a)" refers to H(C$_5$H$_6$)H; "(7b)" refers to HOOC(C$_5$H$_6$)COOH; etc. Other groups of compounds will be similarly referenced.

The chlorination of bicyclo[1.1.1]pentane (7a) is known to lead to a mixture of products in a low yield. The inventors have achieved direct chlorination of 1,3-dibromobicyclo[1.1.1]pentane (7c) to yield the tetrahalo derivative shown below as (8a) quite cleanly.

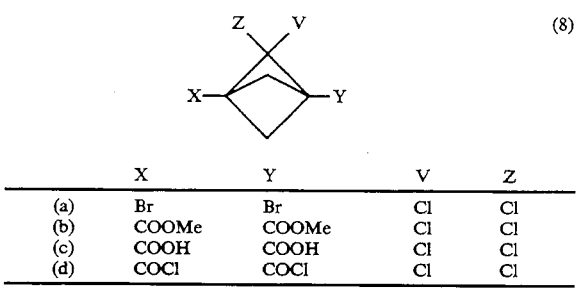

| | X | Y | V | Z |
|---|---|---|---|---|
| (a) | Br | Br | Cl | Cl |
| (b) | COOMe | COOMe | Cl | Cl |
| (c) | COOH | COOH | Cl | Cl |
| (d) | COCl | COCl | Cl | Cl |

The inventors have also chlorinated various other 1,3-disubstituted[1.1.1]pentanes to yield the dichloro derivatives (8b), (8c), and (8d). Thus, an opening for the synthesis of bridge-substituted derivatives of [1.1.1]propellane is provided by the present invention.

Several classes of polymers based on [1.1.1]propellane are represented schematically in FIGS. 1–5.

The polymer that resulted from the inventors initial experiments is represented in FIG. 1. A rough estimate of the length of the average rod 50, based on the intensity of the end group signals in MAS $^{13}C$ NMR spectra, suggested that it contained about 20 bicyclo-[1.1.1]pentane units.

Figure 2:
FIG. 2 is a diagrammatic illustration of a poly[1.1.1]propellane telomer which is singly end functionalized with a short end group.
Figure 3:
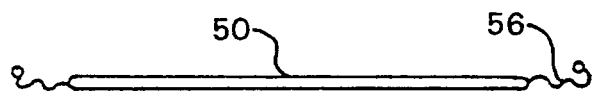
FIG. 3 is a diagrammatic illustration of a poly[1.1.1]propellane polymer which is doubly end functionalized with floppy end groups.
Figure 4:
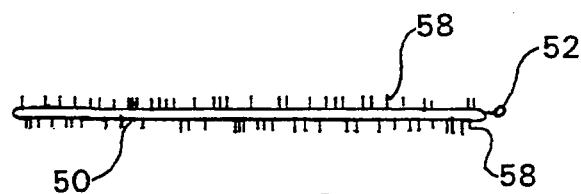
FIG. 4 is a diagrammatic illustration of a poly[1.1.1]propellane which is substituted at a plurality of bridge carbon atom.
Figure 5:
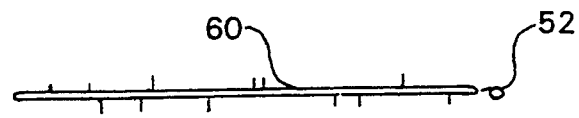
FIG. 5 is a diagrammatic illustration of a copolymer based on [1.1.1]propellane with a plurality of bridge carbon atoms being substituted.

It is believed that more tractable polymers are obtainable by several means, e.g.: (i) reducing the molecular weight to produce a telomer as shown in FIG. 2, and/or changing the end group 56 to produce a polymer as shown in FIG. 3 by control of the radical polymerization process; (ii) introducing Substituents 58 into [1.1.1]propellane before polymerization to produce a polymer as shown in FIG. 4 or copolymerization to produce a polymer 60 as shown in FIG. 5.

The intractability of the polymers appears to increase with increasing molecular weight. Low polymers or high oligomers may be tractable, yet may still have valuable properties. Judicious choice of the chain transfer agent and its concentration may serve to control molecular weight, and in addition, provide a sizeable end group (e.g. 56 in FIG. 3) which could modify the properties of such polymers.

Another way to avoid problems concerning the insolubility of the polymers would be to grow the polymers electrochemically on a surface from a [1.1.1]propellane solution.

Some of the end groups (e.g. 52 in FIG. 1) for which telomerization has already been observed by the inventors, such as CH(COOEt)$_2$, C(COOEt)$_3$, COOMe, etc., lend themselves readily to variations. For instance, the use of long alkyl chains in a malonate could yield more soluble polymers:

$$CH_2(COOC_{16}H_{33})_2 + (1) \longrightarrow \quad (G)$$

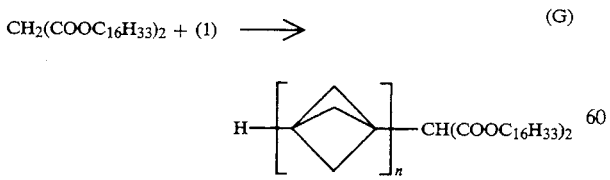

A feasible way to control molecular weight is to use anionic polymerization. Experiments by the inventors indicate that strong nucleophiles (such as n-BuLi) can polymerize [1.1.1]propellane under certain conditions. It is believed that substituted derivatives of [1.1.1]propellane can be used to produce homopolymers or copolymers that exhibit a lower degree of crystallinity, thus enhancing the solubility of the polymer, and possibly introducing other interesting properties.

It is believed that substituted propellanes will be accessible from the diacid (5b), a starting material that can be synthesized via the present invention to use on a large scale.

It is believed that tractable materials will result when [1.1.1]propellane is copolymerized with other compounds, e.g. styrene, acrylate, and methacrylate monomers:

$$nPhCH=CH_2 + m\,(1) \longrightarrow \quad (L)$$

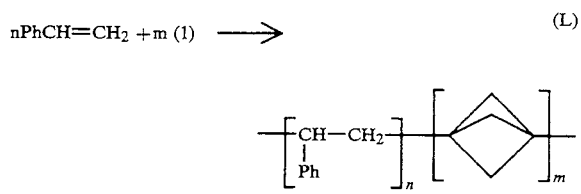

It is believed that alternating type copolymers with [1.1.1]propellane are also achievable. For example, copolymerization with maleic anyhdride (which does not homopolymerize) should produce the following:

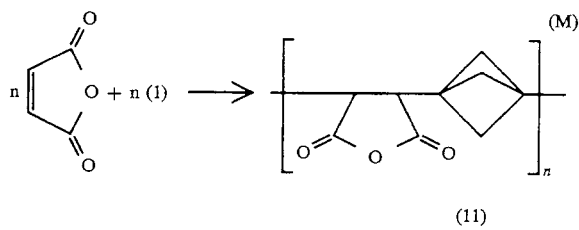

(11)

Such a polymer (11) is anticipated to be soluble due to the great increase in polar groups, and to be reactive due to the anhydride structure.

Another anticipated way of combining [1.1.1]propellane with other units in the backbone is the use of oligomer building blocks in polycondensation. It is expected that access to bifunctional low molecular weight oligomers (e.g. 5–20 cages per chain) will be gained via chain transfer techniques. The transfer agent and/or initiator provide end groups that it is anticipated can be modified to produce macromers. For example:

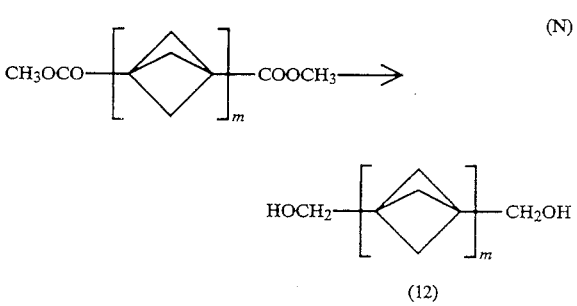

(12)

Subsequent polycondensation may then be carried out, for example to produce polyurethanes:

$$n(12) + nOCN-R-NCO \longrightarrow \quad (O)$$

-continued

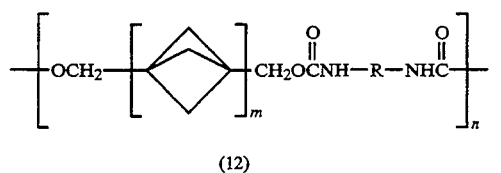

(12)

Once again, there are numerous possibilities for the generation of 'hard' and 'soft' segmented polymer chains.

It is also believed that the diacid (5b) can be used to synthesize polyesters, polyamides, etc:

 (P)

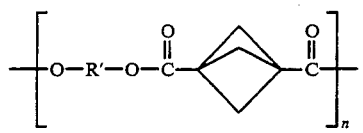

Various other derivatives of the type (7) may be used, such as glycols, diamines, etc.:

 (Q)

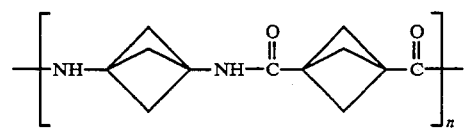

Once again, such material should be soluble.

Another interesting aspect of the present invention is provided by anionic polymerization. Sequential addition of another monomer, such as a conjugated diene, to a living polymer should result in AB block copolymers. Should anionic polymerization be feasible, the use of difunctional initiators could yield ABA block copolymers with either rigid central or end blocks. Such structures are of well known industrial importance.

Another method of preparing poly[1.1.1]propellanes provided by the present invention includes growing the telomer or polymer on a surface electrochemically. In this embodiment, an electrode is immersed in a solution containing [1.1.1]propellane, whereby the bicyclo[1.1.1]pentane rings link to the surface and to other linked rings to grow poly[1.1.1]propellanes. Preferably, the solution is a hydrocarbon solution to avoid undesired reactions of the radicals with the solvent. The length of the chains can be controlled by reaction conditions. This embodiment avoids the problem of insolubility of poly[1.1.1]propellanes, since the compounds are grown directly on a solid surface, and thus need not be soluble.

Other Potential Uses (i) Resists. One anticipated utility of the [1.1.1]propellane based polymers is as positive resists. It is believed that the high energy content of the bicyclo[1.1.1]pentane rings, combined with the instability of cations derived from the bicyclic ring system, make the polymers suitable for e-beam and X-ray resists, photo resists, and thermal resists.

Since destruction of the bicyclo [1.1.1]pentane cage by radiation is expected to cause chain scission, it should be necessary to include only a few percent of cage structures in another polymer structure to produce an effective resist. Since low percentage of propellane units in the backbone of the parent polymers is anticipated to affect the solubility characteristics of the latter only minimally, the coating of the resist should be feasible.

(ii) Optical storage media. Since poly[1.1.1]propellane demonstrates a dramatic weight loss at about 300° C., materials of this kind (with suitable doping) are anticipated to be useful permanent optical storage media for ablation from a thin polymer layer. Unlike the presently used thin layers of tellurium alloys, the polymers provided by the present invention are highly stable in air. The suddenness with which the decomposition sets in provides the advantages that the polymer layer will be stable to bake-out up to around 250° C. and to low-level intensities of reading light, yet ablate readily just above 300° C., leaving a little, very dark residue with essentially no reflectivity. Thus, for example, a layer of poly[1.1.1]propellane may be deposited on an optical recording surface, and high-temperature beams may be applied at selected locations to create craters which may serve as optical recording/storage sites.

It is advantageous to use a soluble polymer for this purpose, both for the ease of spin-coating and for the incorporation of a dye, which will be required to assure high absorbance in the near IR region where diode lasers typically operate. Such dyes as 1,1,5,5-tetrakis(p-dimethylaminophenyl)-2,4-pentadien-1-ol perchlorate (lambda$_{max}$ at 830 nm, 630 nm), and 1,5-bis-(p-dimethylaminophenyl)-1,5-diphenyl-2,4-pentadien-1-ol perchlorate (lambda$_{max}$ at 823 nm, 525 nm), can be used if they are accepted in sufficient amounts into the polymer. In view of their high solubility in chlorinated polymers, use of chloro substituted polymers are preferred.

(iii) Piezoelectrics. Crystalline polymers, such as polyvinylidene fluoride, which contain strongly polar groups which may be oriented to form electrets by thermal and electrical treatment exhibit piezoelectric properties. It has recently been demonstrated that polymers which have a monocyclic repeat unit and contain a polar group posses piezoelectric properties as well. A poly[1.1.1]propellane containing a polar group, such as a halo or cyano substituent, is thus anticipated to be an ideal candidate for a piezolectric polymer.

(iv) Electron and Energy Transfer Rates. Polymers based on [1.1.1]propellane having electron donor/acceptor and functional groups represent an interesting series of spacers for measuring the rates of electron or energy transfer as a function of the number of intervening bonds and of interposed superexchangers [e.g., C=C$_m$, aromatics, lateral substituents]. For example, the following poly[1.1.1]propellane may be used:

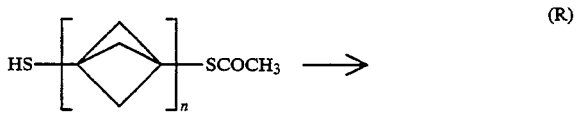 (R)

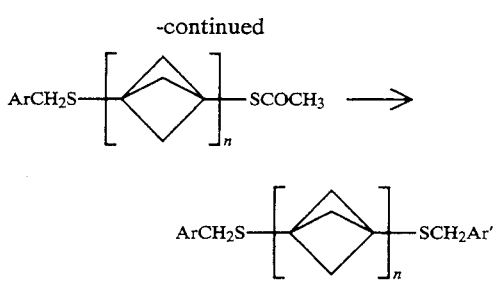

Electron translocation rates in the radical anions may be measured e.g., by pulsed beam radiolysis. Double strands, in which an additional chain which is not necessarily rigid in itself [e.g., oligosilane or —(O-metal)$_n$—] is strung along a beam, can be used to measure the transfer rate increments due to more highly conducting chains of bonds.

(v) High Energy Materials. Due to the high strain energy of the bicyclo ring units, it is believed that such telomers and polymers based on [1.1.1]propellane have application as high energy materials.

1. Molecular "Tinkertoy" Construction System

One embodiment of the present invention provides for the use of telomers and polymers based on [1.1.1]propellane in a system for building molecular structures. Building blocks are provided for a molecular-size mechanical construction set (e.g. rigid molecular building beams having terminal linking connectors for connecting the beams, etc.), permitting the assembly of novel classes of materials. Such materials may be attached to well-defined surfaces, preferably metal surfaces.

Figure 6:
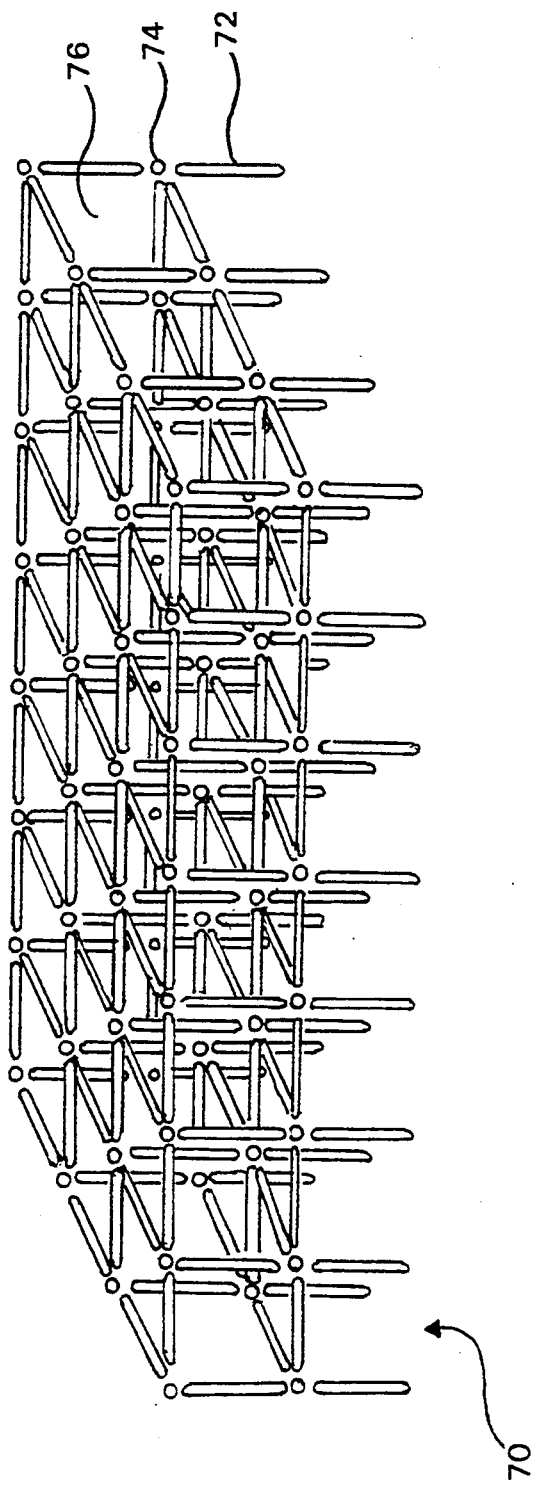
FIG. 6 is a diagrammatic isometric view of a molecular scaffolding structure.

In a preferred embodiment of the present invention, a scaffolding type molecular structure 70 as shown in FIG. 6 is provided. Insertion of straight beams 72 between the lattice points of the rigid beam connecting units or connectors 74 produces an "exploded" solid 70 with potentially very large regular voids 76 accessible to counterions, small solvent molecules, etc. The electric and magnetic properties of the lattice points and of the rigid beam connectors 74 can be controlled by their chemical nature and length. The structures may self-assemble by spitaxial growth on a regular surface, or as a result of a suitable choice of the size of counterions located in the voids 76. They may be amenable to Merrifield-type synthesis in thin layers, with alternating layers of one and another metal, etc.

Figure 7:
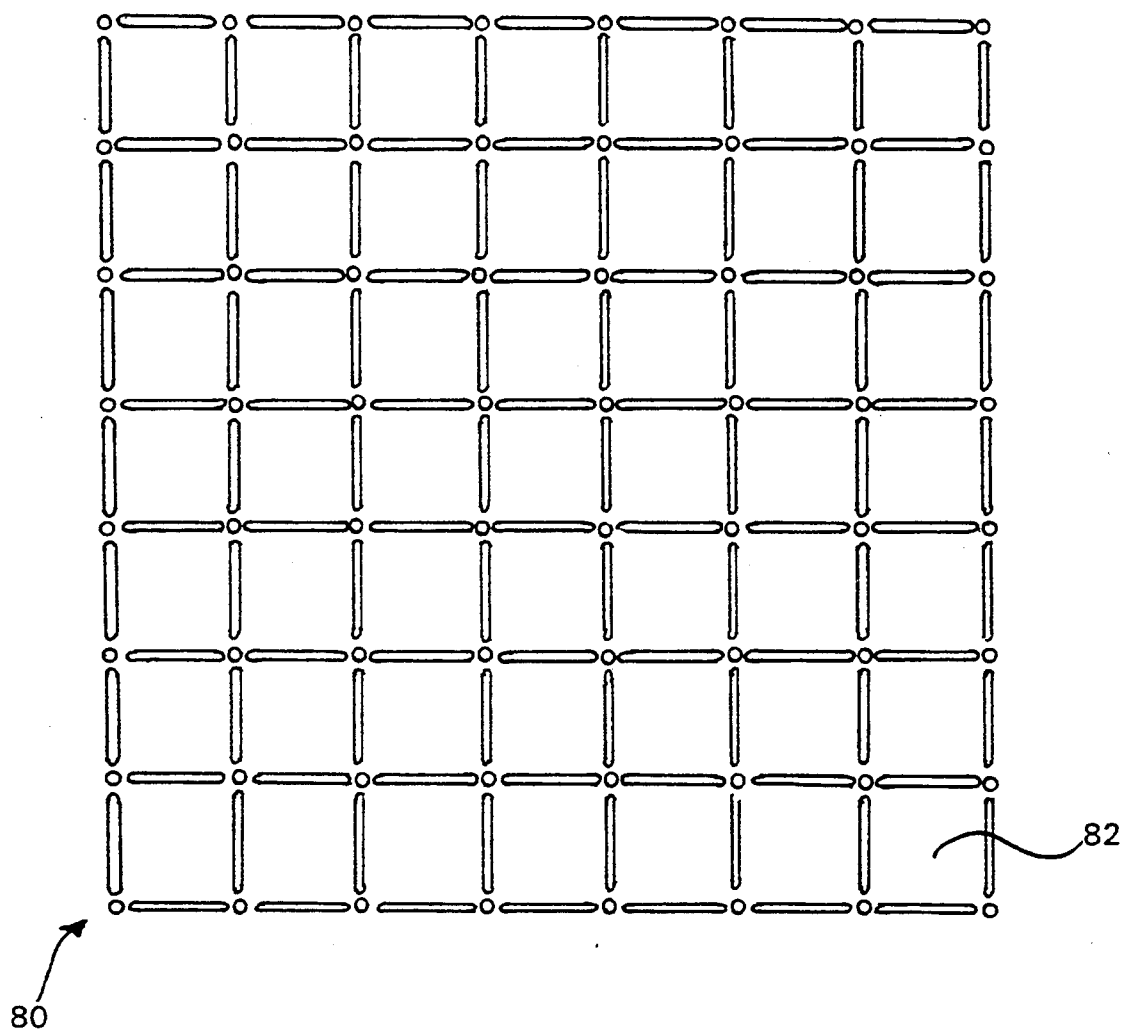
FIG. 7 is a diagrammatic top view of a molecular net structure.
Figure 8:
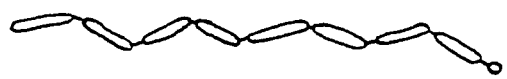
FIG. 8 is a diagrammatic illustration of a molecular whip structure having molecular beams interconnected with short connecting units.
Figure 9:
FIG. 9 is a diagrammatic illustration of a molecular whip structure having molecular beams of varying length interconnected with short connecting units.
Figure 10:
FIG. 10 is a diagrammatic illustration of a molecular whip structure having molecular beams interconnected with floppy connecting units.
Figure 11:
FIG. 11 is a diagrammatic illustration of a molucular whip structure having molecular beams of varying length interconnected with floppy connecting units.

In another embodiment, a two-dimensional net or sieve 80 as shown in FIG. 7 with holes 82 of controlled size is provided.

The molecular structures provided by the invention are capable of nearly infinite variation by attachment of tethered functional groups onto the straight beams, providing an opportunity for blocking the voids by cross-linking, controlled reversibly (e.g., 2-SH —S—S—) or irreversibly (e.g., photochemical chain scission). This offers dynamic control over the size of molecules capable of diffusing through the "exploded" solid, say to an electrode, to a catalyst, etc.

In yet another preferred embodiment, linear polymers are provided. Referring to FIGS. 8–11, these polymers result from the insertion of straight rigid beams between lattice points on a line. For example, molecular cables or whips composed of several interconnected strands may be built. Some strands can be proton-conducting (e.g. via series of hydroxy or amino substituents) or electron- or ion-conducting (e.g. via chain of metal or metal oxide containing substituents). Insertion of these structures across membranes or other layers can yield more complex assemblies. Various forms of copolymerization may be used to incorporate oligomeric building beams into the backbone, either in a regular fashion (see FIGS. 8 and 9), or randomly (see FIGS. 10 and 11), separated either by short segments of the backbone (see FIGS. 8 and 10) or by long segments (see FIGS. 10 and 11).

The bridge carbons of the bicyclo[1.1.1]pentane units of a poly[1.1.1]propellane telomer or polymer can be functionalized to construct a molecular ladder structure of two periodically connected molecular wires. For example, such a ladder having the partial formula (13) can be constructed:

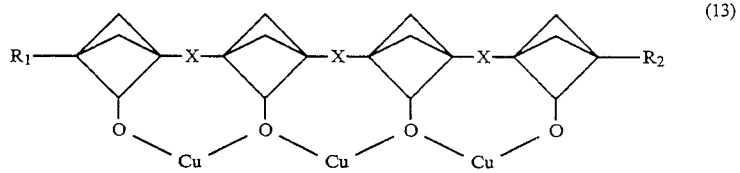

Where $R_1$ is an end group capable of one electron oxidation, and $R_2$ is an end group capable of one electron reduction.

In this structure, the "wire" comprised of the bicyclo ring units acts an an insulator while the "wire" comprised of the copper atoms acts as a conductor for electron transfer between the terminal substituents $R_1$ and $R_2$.

Figure 12:
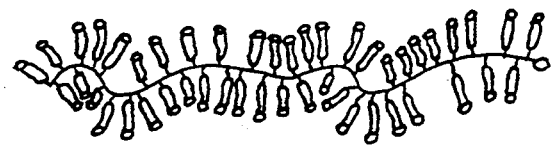
FIG. 12 is a diagrammatic illustration of a molecular comb structure.

The low-molecular weight oligomers of [1.1.1]propellane functionalized on one end can be used to produce comb-like polymers with rigid-rod "teeth", as shown in FIG. 12. Two modes of attachment of the beams as "teeth" are anticipated.

In the first, the attachment is through carbon atoms and requires the attachment of an olefinic residue to the oligomer. For example:

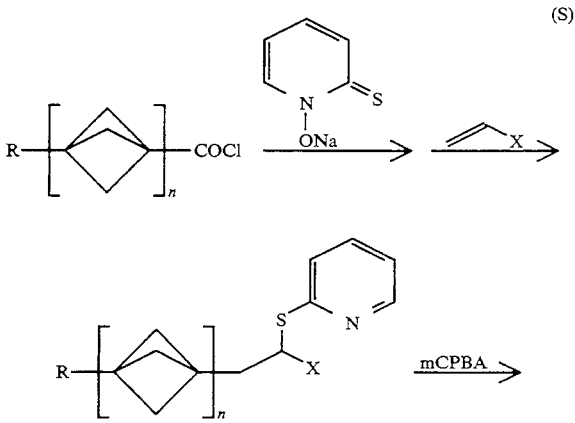

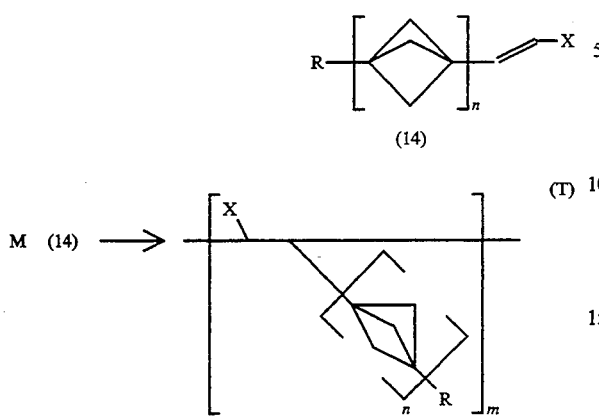

The starting material (R=H) can be obtained from the already available acid. Other choices of R may yield comb-like polymers capable of further transformation and cross-linking (e.g., for R=COOMe, by condensation with a glycol or a diamine).

The second mode of attachment is through a heteroatom. The inventors believe that the oligomeric units may be attached to a preformed functionalized polymer chain, such as poly(vinyl alcohol), to wit:

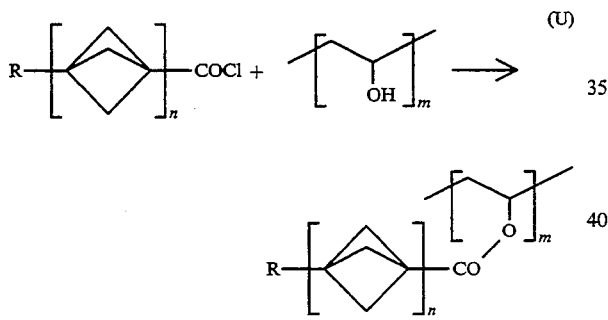

Alternatively, it is believed that an unsaturated monomer, such as a methacrylate, attached at one end of the oligomer may be polymerized, e.g.:

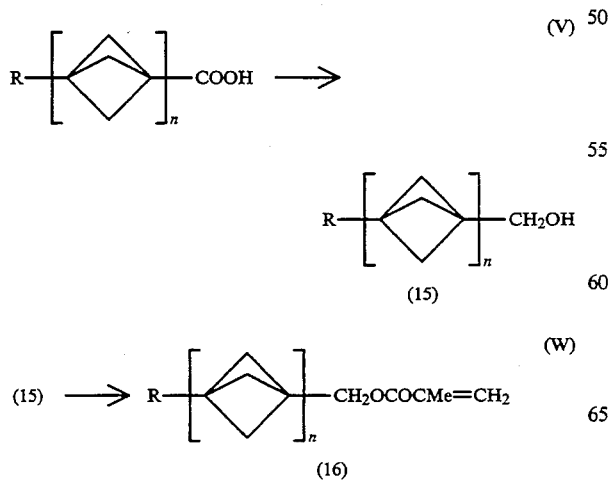

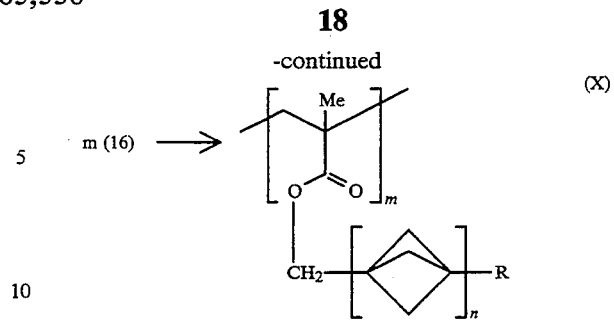

Figure 13:
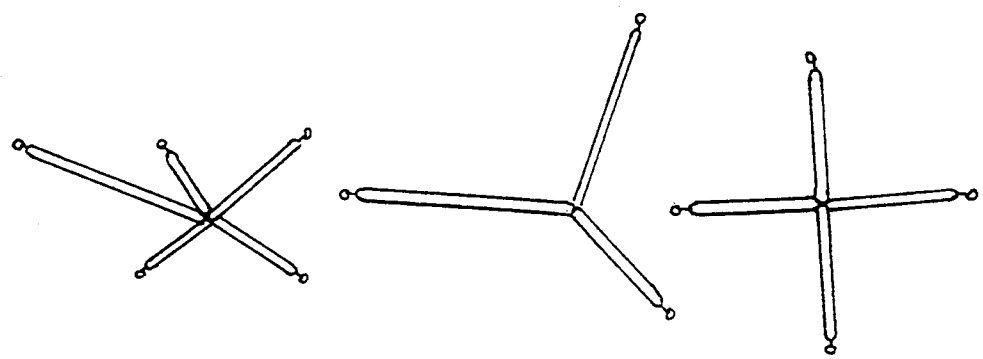
FIG. 13 is a diagrammatic illustration of molecular star structures.

Star-like polymeric structures as provided by another embodiment and shown in FIG. 13 are of considerable theoretical interest. Access to star-like polymers is anticipated by the use of anionic polymerization of [1.1.1]propellane and polychlorinated silanes, disilanes or trisilanes as terminating agents.

Another embodiment provides a molecular windmill, wherein controlled motion is offered by excitation of vibrations and rotations with radiation, ordinary photochemical events such as cis-trans isomerization of double bonds, temporary charge separation in donoracceptor structures, etc.

Molecular windmills in accordance with the present invention comprise a molecular building beam attached at one end to a surface (e.g. metal) and at the other end to a metal connecting unit having a plurality of accepting sites. A plurality of flat ligand "wings" are attached to the metal connecting unit, the wings being attached angularly in relation to each other, preferably perpendicularly.

For example, the following molecular windmill can be constructed:

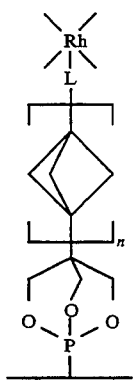

where L is a connecting group or ligand.

The wings attached to the Rh are generally flat or nearly flat ligands. For example, they could be the following:

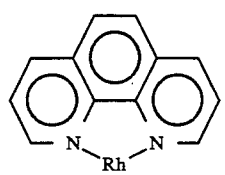

The molecular wings may be artificially rotated by, e.g., a helium stream. It is believed that if the wings are oppositely charged, then their rotation will produce a microwave.

Preferably, the molecular building beam forming the base of the windmill is attached perpendicularly to the support surface for structural stability. Alternatively, for even greater structural stability, three or more beams could be attached to the surface as "legs" of the windmill. In this embodiment, each beam is attached at one end to the solid surface, and at the other end to the same metal connecting unit either directly or via another connecting group.

Applicants believe that molecular structures as provided by the present invention are applicable to many uses. In addition to the uses mentioned earlier, Applicants feel that the "Tinkertoy" structures may be useful in the field of microelectronics. For example, molecular sized electric motors and sensors may be constructed. Structures having voids between the beams may be used as inclusion complexes to house ions within the lattice, or as molecule sieves to purify gases. Such structures could also be used as molecular sieves in solution to prevent undesired passage of certain compounds or complexes therethrough. Thus, for example, the sieve could function as a barrier to protect a catalyst.

Straight, cheap, and readily accessible rigid molecular building beams are preferably used in the present system. They are preferably stable in air and otherwise chemically resistant well above room temperature, available in a variety of finely graded lengths, transparent down to the vacuum UV, electrically insulating, and yet available not only in a form functionalized in a preselected manner at both ends, but also in forms containing one, several, or many additional pre-selected substituents at specified points along their length.

Such molecular building beams are provided by the present invention in the form of oligomers of [1.1.1]propellane. For example, such oligomers (2) may have the following structure:

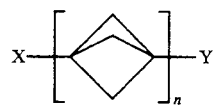

(2)

|  | X | Y |
|---|---|---|
| (a) | SCOCH$_3$ | SCOCH$_3$ |
| (b) | H | COOR |
| (c) | COOR | COOR |
| (d) | H | COOMe |
| (e) | H | COOH |
| (f) | H | CH(COOEt)$_2$ |
| (g) | H | C(COOEt)$_3$ |
| (h) | H | CH(CN)$_2$ |
| (i) | H | C(Ph)(COOEt)$_2$ |
| (j) | H | CH(COMe)COOMe |
| (k) | H | CH(CN)COOMe |
| (l) | H | P(O)(OEt)$_2$ |
| (m) | COOH | COOH |
| (o) | Br | Br |
| (p) | PhCH$_2$ | Br |
| (q) | SBu | SBu |
| (r) | SAC | SAC |
| (s) | SH | SH |

Large amounts of telomers (2) are formed by radical additions to [1.1.1]propellane and can be separated, and can be functionalized at one or both ends. For example, telomer (2a) where n=4 can be formed. Monoesters (2b) can be chlorocarbonylated on the free end to yield the diesters (2c).

The telomers of [1.1.1]propellane fulfill the requirements for the straight beams of the molecular "Tinkertoy" construction set in accordance with the present invention. In spite of their high strain energy (on the order of 68 kcal/mol per bicyclo[1.1.1]pentane unit), they are stable up to 250°–300° C. X-ray analysis indicates that the increment length is approximately 3.35 Å.

In a preferred embodiment, doubly functionalized molecular building beams are provided having metal ligating groups on both ends, ready for the use of dative bonds to transition metal atoms as molecular connecting units. Attachment of beams in a linear orientation with respect to the metal 1Ag and is provided when X and/or Y=CN, NC, C(CH$_2$O)$_3$P, C(CH$_2$CH$_2$)N CH(COCH$_3$)$_2$, COOH, CSSH, C(CH$_2$SH)$_3$, etc.; attachment in an angular orientation is provided when X and/or Y=SR, PR$_2$, NR$_2$, etc.

In an alternative embodiment, covalent connections are constructed. This may be accomplished by providing at least one electrophilic linking group (such as C(CH$_2$O)$_3$SiCl for linear and SO$_2$Cl, CH$_2$Br, COCl, etc., for angular attachment) on a plurality of beams. Such beams may be combined with a plurality of beams having at least one nucleophilic end group (such as amino). Nucleophilic linking groups may be used for linear [e.g. C(CH$_2$CH)$_3$N] or angular (e.g. CH$_2$NH$_2$, CH$_2$Li) attachment to electrophilic linking groups. Alternatively, the beams with electrophilic linking groups may be combined with nucleophilic connectors, such as aromatics, metal complexes of C$_5$H$_5$—, boranes such as B$_{12}$H$_{12}{}^{2-}$, etc. A further alternative provides for the beams having nucleophilic linking groups being attached to electrophilic connecting units, such as BCl$_3$, SiCl$_4$, PCl$_3$, etc.

In still another embodiment, molecular beams are provided having charged end groups, such as SO$_3$— or NR$_3$+. This provides the advantage of an essentially non-directional mode of attachment by electrostatic interaction.

By way of example, polysilanes may be built using the molecular Tinkertoy system of the present invention. Polysilanes are believed to be useful as photoresists. Oligosilane chains may be racked onto the molecular beams of the present invention to fix the desired conformation. For example, a double mercaptan molecular beam can be converted via the following:

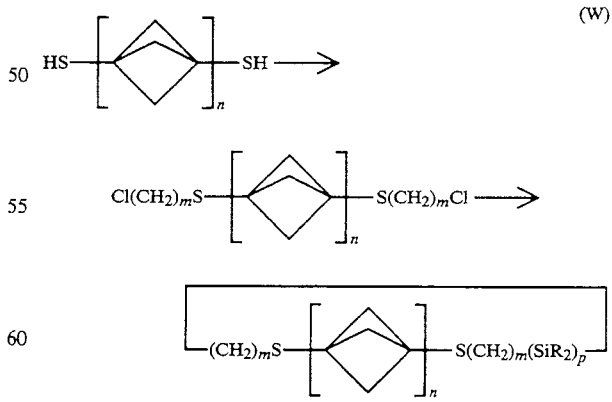

(W)

In a preferred embodiment, a first layer of molecular beams are anchored to a flat surface in an epitaxial fashion. Metal atoms from various sources may be used as anchor sites, such as metal atoms of a monolayer of a metallophthalocyanine, of under-potential-deposited metal atoms on an electrode, islands of vapor-deposited metal atom clusters, and other regular surface patterns.

EXAMPLES

The following examples are designed to illustrate certain aspects of the present invention. However, they should not be construed as limiting the claims thereof.

Example 1

[1.1.1]propellane can be prepared from methallyl dichloride. The inventors have detected the formation of numerous telomers under radical addition conditions, e.g. (2d)–(2l), wherein $n=1$–4 or 5 and isolated many of them in pure state. Their relative amounts have depended on the choice of reactant concentrations. Chlorocarbonylation of (2d), $n=2,3$ has yielded derivatives of (2m). Some of the attempted telomerization reactions did not proceed smoothly. E.g., the reaction of $PhCH_2Br$ with (1) yielded some $(2o, n=2)$, and bibenzyl in addition to $(2p, n=1)$.

Efficient preparation of (2d) seems to require ether-free solutions of (1), obtained in a 15–30% yield based on methallyl dichloride by substituting TMEDA for ether in the Szeimies synthesis. In a typical procedure, a 1.4M solution of (1) in pentans (65 ml) reacted with methyl formate (800 ml) upon irradiation in the presence of benzoyl peroxide (0.4 g). The individual telomers (2d) were separated by crystallization of the acids and potassium salts and by sublimation. Based on methallyl dichloride, the overall three-step yields of purified materials were about 3–6% for $n=1,2$, about 2–4% for $n=3,4$, and about 1–2% for $n=5$, with about 3% of (1) accounted for as higher molecular weight material. It is possible to find reaction conditions under which only the monomer ($n=1$) is formed. At low concentrations of methyl formate and also under anionic polymerization conditions (n-butyllithium, 2–25%), practically only a (2d) polymer was obtained (unoptimized yield, about 50%).

Example 2

The telomers (2) have very high melting points and thermal stability (up to about 300° C.), considering their high energy content (the strain energy of bicyclo[1.1.1]pentane is about 68 kcal/mol). Differential scanning calorimetry on a sealed sample of $(2d, n=4)$ showed a decomposition exotherm at about 320° C. (145.7 kcal/mol). The (2d) polymer decomposed violently at 290° C. with approximately 80% weight loss. In keeping with the high melting points, the solubility of the higher telomers was poor and no solvent for the (2d) polymer was found. Its X-ray diffraction pattern showed a high degree of crystallinity. Its solubility was increased dramatically upon extensive chlorination. Thus, it is believed that substitution will improve the solubility of all the telomers.

Example 3

X-ray structure analysis on $(2d, n=2)$, and $(2o, n=2)$, yielded an inter-ring C—C bond length of about 1.48 A, and a bridgehead-bridgehead separation of about 1.9 A. In $(2a, n=3)$, the inter-ring distances were even shorter, about 1.47 A. Neighboring staffs appeared parallel and meshed An the crystal, with axes only about 4.6 A apart. This very efficient packing is presumably responsible for the high melting points.

Example 4

The salts of the acids (2b) were surface active. In the concentration range of $1.4 \times 10^{-2}$ to $3 \times 10^{-4}$M, the surface tension of an aqueous solution of the potassium salt of $(2b, n=3)$, followed gamma $= -17.7$ log $c - 0.2$ dyn/cm (107 $A^2$ of surface area per molecule). Langmuir-Blodgett films were prepared using the $Cd^{2+}$ salt of $(2b, n=3)$(45 $A^2$/molecule).

Example 5

The NMR spectra of the "staffs" showed each equivalent class of $^1H$ and $^{13}C$ nuclei up to $n=5$. Large bridgehead-bridgehead coupling constants were attributed to transannular orbital interactions. E.g., in $(2l, n=2)$, $^7J[^{31}P^1H]$ was 1.7 Hz. The CP-MAS $^{13}C$ NMR spectrum of the (14d) polymer consisted of a peak at 50.8 (bridge), a sharp peak at 40.3 (bridgehead) and weak end-group signals at 169.7 (carbonyl) and 27.8 (methine).

Example 6

Preparation of Propellane Solutions

Synthesis of 1,1-bis(chloromethyl)-2,2-dibromocyclopropane (18) on a 2 mole scale produced a consistent 29–31% yield in production of rigorously pure material. Preparation of [1.1.1]propellane from the tetrahalide precursor (18) was best achieved using MeLi in diethyl ether. ("Procedure A"). Ether free propellane is available from an alternate procedure using BuLi and TMEDA with (18). ("Procedure B").

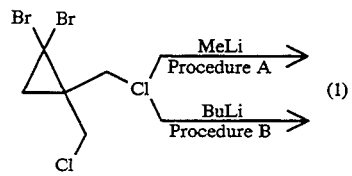

(18)

After distillation of the crude solution (40–80% yield), 1.5M [1.1.1]propellane in pentans, free of halides, was produced in 30–60% from (18). The yield was probably varied by anionic polymerization of propellane.

Both solutions were stable showing only small changes in concentration over long periods under oxygen-free conditions at a freezer temperature of about $-15°$ C.

Example 7

Preparation of Sulfur Compounds

Photolysis of one equivalent of symmetrical alkyl or acyl disulfides in an ethereal solution of propellane gave at least four oligomers. As expected, relative yields of oligomers were strongly dependent upon concentration of starting material. Steric hinderance of the RS radical as from t-butyl disulfide, or pivaloyldisulfide, completely prevented formation of any disulfide derived product. In contrast, aryl disulfides, for instance the parent diphenyldisulfide (and dipenyldiselenide), produced largely the first adddot.

Aceticthiol acid ($CH_3COSH$) adds to (1) giving only a first adduct, i.e. acetylthiobicyclo[1.1.1]pentane. This compound is a convenient precursor for synthesizing the corresponding mercaptan and disulfide.

Example 8

Halides

Bromine and iodine add to propellane, abeit in small yield, due to rapid decomposition. Even isolated products had to be rigorously purified and stored in the dark at low temperature. The more useful adducts, however, were derived from additions of organic halides. Alkyl iodides, as in the case of the iodine adduct, provided unstable products containing no oligomers. Generally yields were moderate (with the low output exception of MeI). Unsubstituted or withdrawer substituted aryl iodides were coaxed to produce a disubstituted bicyclopentane with Procedure B propellane. However, accompanying side reactions such as hydrogen abstractions made the syntheses less than optimal, and no products were observed from donor substituted aryls such as iodoanisole. Behavior of homologous alkyls seemed to parallel stability of the radicals formed from bond homolysis.

An unusual iodide transfer reaction was observed in the photolysis of 1,3-diiodobicyclo[1.1.1]pentane in the presence of propellane in pentane. 3,3'-bisiodo[2]staffane, was the sole product, formed largely as a precipitate, which was not induced to form higher oligomers.

Alkyl bromides were largely inert to photochemically initiated addition to propellane, except when a particularly stable radical was formed, as in the case of t-BuBr and benzylbromide, or alpha-carbonyl activated bromide such as methylbromoacetate or -malonate. As with alkyl iodides, no oligomers were formed. Bromide transfer reactions with 1,3-dibromobicyclo[1.1.1]pentane in the presence of [1.1.1]propellane were not achievable. However, reaction with benzylbromide gave 3,3'-dibromo[2]staffane as a side product.

Example 9

Physical Properties of Oligomers

NMR shifts varied in a predictable pattern as the bicyclopentyl repeating units were added incrementally. Typically, proton or carbon resonances shifted upfield the further the atoms were located from the ends of the molocule.

X-ray structures established in the monosubstituted case that interring distances were considerably shorter than normal C—C bonds. 3,3'''-bisacetylthio[3]staffane displayed a tight interlocking packing arrangement with an interplane distance of about 4.6 A.

Examples 10–25

Boiling points in these examples were uncorrected. Melting points were determined by Boetius PHMK05 apparatus with microscope attachment at a warm up rate of 4° C./min. or in sealed capillary and were uncorrected. NMR spectra were run on a Nicolet NT-360 in CDCl3 as a solvent unless specified otherwise. Infrared spectra were recorded on a Nicolet 60SXR FTIR.

1.4M solution of methyllithium in ether (halide free), bromoform of 96% purity and 3-chloro-2-chloromethyl-1-propene of 94% purity were purchased from Aldrich Chemical Co. and used with no further purification. All operations and reactions involving [1.1.1]propellane were performed under an atmosphere of dry argon. Photochemical reactions were carried out at ice bath temperature, using a 450 W medium pressure Hanovia mercury lamp; the solution was contained either in a round bottom pyrex flask or in a pyrex immersion photolysis apparatus. A typical run scale was 0.1 mole of 1,1-bis(chloromethyl)-2,2-dibromocyclopropane (unless specified otherwise) and the etheral solution of the propellane was used for reactions with no further separation or puridication soon after generation. Preparative scale gas chromatography was carried out on 10% SE-30, 6 ft column. X-ray structures were determined on a Suntex Diffractometer equipped with a graphite monochromator.

Example 10

1,1-bis(chloromethyl)-2,2-dibromocyclopropane 1000 ml of 50% sodium hydroxide was added in 10–15 min. to a vigorously stirred mixture of 370 ml (4.24 mol) of bromoform, 250 g (2.0 mol) of 3-chloro-2-chloromethyl-1-propane, 10 g of benzyltriethylammonium chloride, 8 ml of ethanol and 200 ml of methylene chloride. The temperature during the addition as well as later was maintained between 25°–35° C., controlled by lowering the reaction flask in an ice bath. After overnight stirring, 500 ml of methylene chloride was added and the thick black mixture was allowed to separate into layers. The top aqueous layer was removed and the bottom layer was gently washed with 500 ml portions of water. 500 ml of water was then added, well shaken, and left for phase separation. The clear, dark-brown organic phase was separated and the residual emulsion was treated with solid sodium chloride and filtered through Celite which aided separation. All aqueous layers were washed with methylene chloride and the organic extracts were combined, dried over magnesium sulfate, and filtered through Celite. Concentration and vacuum distillation gave 350–380 g of a mixture of starting material and black-brown residue which was distilled on a Kugel-Rohr giving 315–350 g of semicrystalline fraction (65° C./0.45 mm Hg up to 115° C./0.9 mm Hg) containing the product. Crystallization from 400 ml of pentane from a dry ice-acetone bath gave 205–215 g of white wet crystals (mp 38°–41° C.). The crude product was dissolved in 400 ml of penfane, 7.5 g of silica gel was added, filtered and low temperature recrystallized again, giving 171–182 g of product which melted at 44°–46° C. One more crystallization (400 ml of pentane) gave 164–175 g (29–31% yield accounting 94% purity of starting olefin) of pure compound: mp. 47° C. (lit. 45°–6° C.); $^1$H NMR 1.82 (s, 2H), 3.94 (d, J=11.9 Hz, 2H), 3.99 (d, J=11.9 Hz, 2H); $^{13}$C NMR 32.07, 34.07, 35.35, 47.67.

Example 11

[1.1.1]Propellane in Diethylether (Procedure A)

29.7 g (0.1 mole) of 1,1-bis(chloromethyl)-2,2-dibromocyclopropane and 30 ml of pentane were placed under argon in a 500 ml three neck flask equipped with mechanical stirrer, septum, and side arm connected to cold trap. 170 ml (0.24 mole) of methyllithium in ether was added through septum with vigorous stirring, in a period of 10 min. at −78° C. When the addition was complete, the dry ice-acetone bath was replaced by an ice bath. The yellowish reaction mixture was stirred for 1 hr and then all volatiles were vacuum transferred (50 mm Hg) to a dry ice-acetone trap. When almost dry salts appeared in the flask, the vacuum was disconnected and the apparatus was opened to dry argon atmosphere. 210 ml of colorless clear solution was obtained. $^1$H NMR (C$_6$D$_6$) showed signals belonging to: diethylether 1.03 (t, J=7.1 Hz, 6H), 3.25(g, J=7.1 Hz, 4H); methylbromide 2.27 (s); [1.1.1]propellane 1.76 (s); pentane 0.79 (t, J=6 Hz,6H), 1.19 (m, 6H) in the following proportions 100:5.5:3.9:6.25. Concentration of the propellane calculated based on $^1$H NMR spectrum was 3% (by weight).

Example 12

[1.1.1]propellane in pentane solution (Procedure B)

29.7 g (0.1 mol) of 1,1-bis(chloromethyl)-2,2-dibromocyclopropane, 20 ml of N,N,N',N'-tetramethylethylenediamine (TMEDA) and 50 ml of pentane were placed under argon in a 500 ml 4 neck flask equipped with mechanical stirrer, septum, low temperature thermometer, and side arm connector to cold trap. The solution was cooled to −50° C. and 22 ml of 10.0M BuLi were added via cannulation keeping the temperature below −30°-C. When addition was complete, the mixture was stirred for 0.5 hours at −20° C. and H$_2$O added until further addition did not affect the temperature (2 ml). Vacuum transfer at room temperature gave a clear solution leaving a viscous brown liquid. The crude propellane solution (42–75% yield by NMR comparison to theoretical amount of benzene) was cannulated by argon pressure from the −78° C. collection flask to a distillation apparatus featuring a 10 cm Vigreaux column. Keeping the pot temperature below 90° C., a solution of propellane (30% yield) was obtained containing only hydrocarbons.

Example 13

1,3-Dibromobicyclo[1.1.1]pentane.

12.8 g (0.08 mol) of bromine, freshly distilled from P$_2$O$_5$, was added dropwise to a stirred 0.1 mole portion of propellane solution prepared by Procedure A. The resulting mixture was evaporated and an oily yellow residue was crystallized from pentane at low temperature (−78° C.) giving 2.9 g (16% based on bromine) of white crystals (mp 110°–115° C.). Recrystallization gave pure 1,3-dibromobicyclo[1.1.1]pentane: mp. 122° C. (sealed capillary) (lit. mp. 118° C.); $^1$H NMR 2.57 (s); $^{13}$C NMR 30.46, 64.72.

Example 14

1,3-Diiodobicyclo[1.1.1]pentane 11.4 g (0.045 mole) of sublimed iodine dissolved in 100 ml of dry ether were added dropwise to a magnetically stirred 0.1 mole solution prepared by Procedure A. The resulting solution was evaporated and the yellow to brownish crystalline mass dissolved in chloroform and passed through a short silica gel column. To the slightly pink eluent, 10 ml of heptane was added and the solution was evaporated to dryness giving 5.0 g of white crystals of the diiodide: mp. 153° C. dec. (sealed tube); $^1$H NMR 2.67 (s); $^{13}$C NMR −1.80, 68.25; EIMS, m/z (relative intensity) 320(5), 193(40), 128(35), 127(43), 66(100), 65(70); HRMS, m/z (calcd for C5H6I2: 319.85590) 319.85639; Anal. calcd for C5H6I2: C, 18.77; H, 1.89; I, 79.34. Found: C, 18.84; H, 1.90; I, 79.24.

Example 15

1-Bromo-3-t-Butylbicyclo[1.1.1]pentane

A magnetically stirred solution of the propellane (prepared on a 0.05 mole scale via Procedure A), 35 ml of tert-butyl bromide and 0.4 g of benzoyl peroxide was irridiated in a round bottom flask for 10 hr. Evaporation of the solvent and the excess of t-butyl bromide followed by short path distillation gave a semicrystalline fraction. Low temperature crystallization from pentans gave a white product: mp. 80.5°–81.0° C.; $^1$H NMR 0.84 (s, 9H), 2.03 (s, 6H); $^{13}$C NMR 26.45, 31.02, 37.62, 49.65, 55.48; EIMS, m/z (relative intensity) 205(2), 123(12), 107(28), 91(62); HRMS, m/z (calcd. for C9H15: 123.11738) 123.11775; Anal. calcd for C9H15Br: C, 53.21; H, 7.44; Br, 39.34. Found: C, 53.15; H, 7.44; Br, 39.25.

Example 16

1-Benzyl-3-bromobicyclo[1.1.1]pentane and 3,3'-dibromo[2]staffane.

A mixture of the propellane solution (prepared on a 0.05 mol scale via procedure A), 7 ml of benzyl bromide and 0.3 g of benzoyl peroxide was irradiated in a round bottom flask for 15 hr. Solvents were evaporated, excess of the benzyl bromide was distilled of under vacuum (40°–43°– C./0.9 mm Hg) and the residue was short path distilled giving a semicrystalline fraction (80°–10° C./0.6 mm Hg). Crystallization from pentans (or heptane) gave 3,3'-dibromo[2]staffane, which after sublimation (90° C./1.0 mm Hg) gave an analytical sample: mp. 175° C. (dec. sealed capilliary to a brown liquid at 203° C.; $^1$H NMR 2.11 (s); $^{13}$C NMR 36.30, 40.18, 57.90; Anal. Calcd for C10H12Br2: C,41.13; H, 4.13; Br, 54.73; Found: C, 41.17; H, 4.18; Br, 54.64. The filtrate was cooled in dry ice-acetone bath and the resulting white crystals were filtered off. Recrystallization followed by vacuum sublimation gave a sample having the following: $^1$H NMR 2.06 (s, 6H), 2.83 (s, 2H), 7.04–7.08 (m, 2H), 7.18–7.31 (m, 3H); $^{13}$C NMR 41.55, 58.45, 126.29, 128.38, 128.70, 138.33; EIMS, m/z (relative intensity) 157(62), 129(100), 128(36), 117(59), 116(55), 115(94), 91(93), 65(40), 39(35); HRMS, m/z (calc for C12H13: 157.10173) 157.10218.

Example 17

1-Butyl-3-iodobicyclo[1.1.1]pentane

A solution of the propellane (prepared on a 0.05 mole scale via procedure A) and 7 ml (0.053 mol) of 1-iodobutane was irradiated in a round bottom flask for 5 hr (until no more progress was monitored by GC). Solvents were evaporated and distillation of the yellowish residue gave 4.2 g (34%) colorless liquid (bp. 54°–55° C./0.8 mm Hg) which gradually turned brown upon standing: $^1$H NMR 0.87(t, J=7.1 Hz, 3H), 1.16–1.33 (m, 4H), 1.49 (t, J=7.7 Hz, 2H), 218 (s 6H); $^{13}$C NMR 7.8, 13.86, 22.49, 28.91, 31.76, 48.56, 60.64; IR(neat) 837, 1173 cm $^{-1}$; EIMS, m/z (relative intensity) 123(68), 91(30), 81(100), 79(37), 67(47); HRMS, m/z (calc for C9H15: 123.1174) 123.1172; Anal. Calcd for C9H15I: C, 43.22; H, 6.05; I, 50.74; Found: C, 43.06; M, 6.07; I, 50.95.

Example 18

1-Iodo-3-(1-methylpropyl)bicyclo[1.1.1]pentane

The same procedure as in Example 17 substituting 2-iodopropane led to 4.0 g (32%) of slightly brownish liquid (bp. 51°–52° C./0.8 mm Hg) which became brown upon standing: $^1$H NMR 0.79 (d, J=6.7 Hz, 3H), 0.85 (t, J=7.2 Hz, 3H), 0.93–1.03 (m, 1H), 1.34–1.41 (m, 1H), 1.47–1.53 (m, 1H); $^{13}$C NMR 8.29, 11.86, 15.89, 26.48, 36.57, 52.92, 58.91; IR(neat) 829, 847, 1177 cm$^{-1}$;

EIMS, m/z (relative intensity) 128(30), 127(20), 123(18), 81(100), 79(30), 77(25), 67(45), 55(43); HRMS, m/z (calcd for C9H15: 123.1174) 123.1171; Anal. Calcd for C9H15I: C, 43.22; H, 6.05; I, 50.74; Found: C, 42.99; I, 6.05; I, 51.00.

Example 19

3,3'-Diiodo[2]staffane

A 0.1 mole scale run using Procedure B was cannulated into a borosilicate tube containing 0.5 equivalent of 1,3-diiodobicyclo[1.1.1]pentane. Pentane, or branched hydrocarbons were added to dissolve the starting material, then the solution was irradiated with a quartz lamp for 1 hr at 0° C. Product crystallized on the walls of the vessel as the reaction proceeded (followed by GC with <250° C. injector) and was isolated by crystallization at 0° C. and recrystallization from benzene to give clear needles which decomposed slowly on contact with the atmosphere and rapidly in direct sunlight: mp. dec. 120° C.; $^1$H NMR 2.18 (s); $^{13}$C NMR 6.35, 47.49, 59.73; Anal. Calcd for $C_{10}H_{12}I_2$: C,31.11; H, 3.13; I,65.75, Found: C, 31.16; H, 3.16; I, 65.62.

Example 20

1-Iodo-3-phenylbicyclo[1.1.1]pentane 1.28 ml (0.5 e.g.) of iodobenzene were added to a solution of propellane (10 mmol) generated via Procedure B. The solution was transferred into a borosilicate tube and irradiated 1 hr, after which GC analysis of the solution showed three new major peaks. The reaction mixture was reduced in volume, high vacuum applied (40° C./0.2 mm Hg) to remove starting material and 1-iodobicyclo[1.1.1]pentane. After these products were removed, 1-iodo-3-phenylbicyclo[1.1.1]pentane sublimed out of the mixture (40°–50° C./0.2 mm Hg): $^1$H NMR 2.06 (s, 6H); EIMS, m/z (relative intensity) 77(24), 127(25), 128(100), 143(91). Resublimation produced an analytical sample having mp. 64°–65° C. Recrystallization from penfane at 0° C. gave a gummy solid. The liquid was diluted with pentane and recrystallization at −78° C., giving 1-phenylbicyclo[1.1.1]pentane: The solid, a mixture of 1-phenyl]2]staffane and 3-iodo-3'-phenyl[2]staffane by GCMS, was recrystallized from benzene.

Example 21

1,3-Diacetylbicyclo[1.1.1]pentane

A magnetically stirred solution of 0.1 moles of Procedure A propellane and 9 ml of biacetyl were placed in a round bottom flask and photolyzed for 6 hours. The solvents were then evaporated and the residue was distilled on Kugel-Rohr (80°–85° C./0.4 mm Hg) giving 12.1 g of wet yellowish product. Crystallization from 25 ml heptane gave 8.80 g (58% yield) of large clear crystals of 1,3-diacetylbicyclo[1.1.1]pentane: mp. 67°–69° C. $^1$H NMR 2.14 (s, 6H), 2.24 (s, 6H); $^{13}$C NMR 25.79, 43.10, 51.81, 205.01; EIMS, m/z (relative intensity) 152(1),137(11), 109(43), 95(10), 43(100), 39(25), 28(54); HRMS, m/z (calc. for C9H12O2: 152.0837) 152.0839; Anal. Calcd for C9H12O2: C, 71.02; H, 7.95, Found: C, 71.01; H, 7.97.

Example 22

Formation of Telomers: Adducts of diacetyldisulfide and propellane 22.5 ml of diacetyldisulfide (0.5 e.g.) were added to a solution 0.3 moles of propellane in ether made via Procedure A. The solution was irradiated in a round bottom flask for less than 3 hr (to avoid product decomposition). Evaporation of solvent to 40.06 gm crude mixture and refrigeration overnight produced 2.66 gm of oligomers 2,3, and 4 in 20:51:16 ratio by GC after vacuum filtration and wash with cold MeOH. Short path distillation of starting materials and decomposition products (25°–60° C./0.2 mm Hg) recovered diacetyl disulfide. Dilution of the pot residue with an equal volume of methanol and icebath gave 5.31 gm of yellowish solid containing mostly second oligomer. Further recrystallizations and subsequent sublimations (85° C./0.2 mm Hg) produced his acetylthio[2]staffane: mp. 101° C.; $^1$H NMR 2.03 (s, 12H); 2.26 (s, 6H); $^{13}$C NMR 31.16, 37.99, 42.84, 53.35, 196.18; EIMS, m/z (relative intensity) 43(100), 239(.5), 267(.02); Anal. Calcd for $C_{14}H_{18}O_2S_2$: C, 59.54; H, 6.42; O, 11.33, S, 22.70; Found: C, 59.43; H, 6.45; S, 22.61.

From both fractional and gradient sublimations, 3,3''-bis(acetylthio)[3]staffane were obtained: bp. 125° C./0.2 mm Hg; $1^H$ NMR 1.47 (s, 6H), 1.97 (s, 12H), 2.25(s, 6H): $^{13}$C NMR 31.12, 37.62, 37.83, 43.52, 48.38, 53.26, 196.20; Anal. Calcd for $C_{19}H_{24}O_2S_2$: C, 65.48; H, 6.94; O, 9.18; S, 18.40. Found: C, 65.37; H, 6.98; S, 18.47.

Gradient sublimation gave 3,3'''-bis(acetylthio)[4]staffane: $^1$H NMR 2.25 (s, 6H), 1.96 (s, 12H), 1.41 (s, 12H); $^{13}$C NMR 31.22, 37.43, 37.95, 38.25, 43.81, 48.12, 53.39, 196.51; IR CM$^{-1}$; EIMS, m/z (relative intensity) 43(100), 91(10), 341(0.14), 429(0.1); Anal. Calcd for. $C_{24}H_{30}O_2S_2$: C, 69.52; H, 7.29; O, 7.72; S, 15.46. Found: C, 69.60; H, 7.32; S, 15.37.

The higher oligomers decomposed upon heating especially in the presence of impurities to give elemental sulfur and other products.

Example 23

Addition of methyldisulfide to propellane

To a solution of 0.1 mole propellane in ether (Procedure A) was added 9.0 ml of methyldisulfide. (1 eq.) The mixture was photolyzed 3 hr in a round bottom flask (the process was cleaner when carried out in pentane, albeit lower yield.)

Starting material was removed with solvent on the rotary-evaporator and Vigreaux distillation (57° C./0.2 mm Hg) providing 13.0 g (85%) of 1,3-bismethylthiobicyclo[1.1.1]pentane: $^1$H NMR: 1.99 (s, 1H), 2.04 (s, 1H); $^{13}$C NMR 13.69, 40.98, 59.89. Second oligomer was recrystallized from pot residue with methanol/H$_2$O and sublimed to give 4% 3,3'-bis(methylthio)[2]staffane: $^1$H NMR 1.76 (s, 2H), 2.05 (s, 1H); $^{13}$C NMR 13.47. GC preparation of the sublimation residue allowed an analytical sample of 3,3''-(bismethylthio)[3]staffane.

Example 24

1-chloro-3-methanesulfonylbicyclo[1.1.1]pentane and 1-chloro-3'-methanesulfonyl[2]staffane A 0.1 mole run using Procedure A was photolyzed in a round bottom flask with magnetic stirring for 6 hours in the presence of 3.9 ml (0.5 eq.) of methane sulfonyl chloride and 0.1 g of benzoyl peroxide. GC shows first and second oligomers. The solution was cooled to ice temperature and filtered to give 2.9 g of off-white powdery solid of second oligomer which is recrystallizable from heptane/CHCL$_3$: $^1$H NMR 2.06 (s, 6H), 2.08 (s, 6H), 2.81 (s, 3H); $^{13}$C NMR 56.24; Anal. Calcd for $C_{11}H_{15}ClO_2S$: C, 53, 54; H, 6.13; Cl, 14.37; S, 12.99. Found: C, 53.45; H, 6.18; Cl, 14.38; S, 13.03.

1-Chloro-3-methanesulfonylbicyclo[1.1.1]pentane was obtained by Kugel-Rohr distillation of the filtrate and recrystallization from heptane: $^1$H NMR 2.54 (s, 6H), 2.859 (s, 3H); $^{13}$C NMR 38.50, 42.14, 47.54, 48.83, 57.10.

Example 25

1-chloro-3-benzenesulfonylbicyclo[1.1.1]pentane 0.025 mole scale of Procedure A propellane synthesis was irradiated with 25 mg of benzoyl peroxide and 0.05 moles, 2 eq. 6.4 ml of benzene sulfonyl chloride for 6 hr. After rotoevaporation and distillation of starting material via Kugel-Rohr (up to 90° C. at 0.5 mm Hg), the yellow, crude product was treated with silica gel, washed with 20 ml heptane, and recrystallized from boiling heptane with toluene added for complete solubilization. A second crop of crystals yielded a total of 3.1 g of 95% pure colorless plates (56% overall yield); mp: $^1$H NMR 2.40(s, 6H), 7.59(t, 2H), C NMR 136.10, 129.33, 57.04, 128.46.

Examples 28–31

Photochemical Synthesis of Bicyclo[1.1.1]pentane-1,3-dicarboxylic Acid

It is believed that the mechanism of the photoaddition of biacetyl to [1.1.1]propellane is represented by the following chain process, where the key step is a beta-fragmentation of an alkoxy radical:

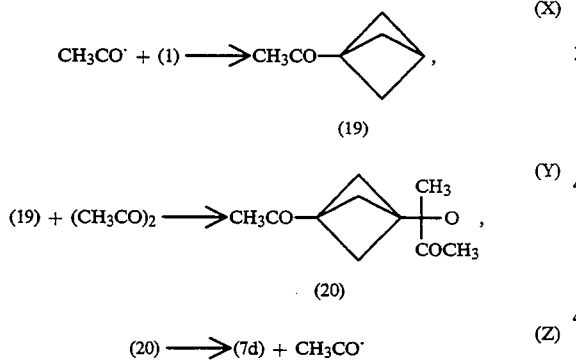

Irradiation of a solution of biacetyl and [1.1.1]propellane in diethyl ether followed by hypobromite oxidation of the resulting diketone (7d) yielded the desired diacid (7b) in an overall yield of 52% based on the starting tetrahalide (18):

In the following examples, boiling points were uncorrected. Melting points were determined using a Boetius PHMK05 apparatus with a microscope attachment at a heating rate of 4° C./min. Melting points taken in a sealed capillary were uncorrected. NMR spectra were run on a Nicolet NT-360 instrument in CDCl$_3$ solvent unless specified otherwise. IR spectra were recorded on a Nicolet 60SXR FTIR instrument. Mass spectra were taken on a 5995 Hewlett-Packard instrument.

Example 26

1,3-Diacetylbicyclo[1.1.1]pentane 89.1 g (0.30 mol) of (18) and 90 ml of pentane were placed in a 1-liter three-neck round bottom flask equipped with a mechanical stirrer, septum and a side arm connected to a dry-ice condenser and flushed with dry argon. With vigorous stirring, 510 ml of a 1.4M solution of methyllithium (Aldrich, salts-free) were added via cannula in 15 min at the dry ice-acetone bath temperature. When the addition was completed the bath was replaced by an ice bath and the stirring was continued for 1 h. All volatiles were then vacuum-transferred to a cold trap equipped with a 1-liter round bottom flask receiver containing a magnetic stirring bar. When almost dry salts appeared in the flask the transfer was discontinued and the apparatus was again filled with argon. The receiver containing the propellane solution was disconnected from the cold trap, stoppered with a saprum and 27 ml of freshly distilled biacetyl were added from a syringe. The solution was stirred at ice bath temperature and irradiated in a Pyrex vessel for 8 h with a 450 W medium pressure Hanovia mercury lamp under dry argon. Volatiles were evaporated and the semicrystalline residue was distilled on a Kugel-Rohr (80°–85° C./0.4 mm Hg), yielding 36.2 g of wet white to pale yellow crystals. Crystallization of the crude (7d) from heptane afforded 26.4 g of pure 4 in a 58% overall yield based on (18). Mp 67°–69° C.; $^1$H NMR delta 2.14 (s,6H), 2.24 (s,6H); $^{13}$C NMR delta 25.79, 43.10, 51.81, 205.01; IR (C-O) 1708; MS, m/z (relative intensity) 152(1, M$^+$), 137(11), 109(43), 95(10), 43(100), 39(25); HRMS, m/z (calcd for $C_9H_{12}O_2$, 152.0837) 152.0839; Anal. Calcd for $C_9H_{12}O_2$: C, 71.02; H, 7.95. Found: C, 71.01; H, 7.97.

Example 27

Bicyclo[1.1.1]pentane-1,3-dicarboxylic acid 26.4 g of (7d) was dissolved in 125 ml of dioxane and added over a period of 2 h to a stirred solution of sodium hypobromite prepared from 65 ml (1.25 mol) of bromine, 140 g (3.5 mol) of sodium hydroxide and 1050 ml of water at 0°–3° C. After the addition of the diketone was completed, the reaction mixture was stirred for 1 h at 0° C., then 3 h at room temperature and finally 1 h at 50° C. Next, 6 g of sodium bisulfite were added and the reaction mixture was extracted with 3×300 ml of chloroform, acidified with 225 ml of concentrated hydrochloric acid and extracted with ether in a continuous extraction apparatus for 30–50 h. The ether was evaporated, the residue was dried under reduced pressure and the crude product was washed with 50 ml of boiling chloroform. Cold suspension of the product was filtered giving 24.6 g (90% yield) of the diacid (7b): mp 305° C. rapid dec, sealed tube (lit. mp >260° C. subl.), $^{13}$C NMR (acetone-d$_6$) 38.08, 53.04, 170.59.

Example 28

Bicyclo[1.1.1]pentane-1,3-dicarboxylic acid via addition of acetaldehyde to [1.1.1]propellane A solution of [1.1.1]propellane in diethyl ether prepared by the above procedure (210 ml, 3% in [1.1.1]propellane according to integrated $^1$H NMR intensities), 150 ml of acetaldehyde and 0.4 g of benzoyl peroxide was stirred and irradiated as above for 6 h. Evaporation of solvents and access acetaldehyde at reduced pressure (at the end, 50° C./0.8 mm Hg) furnished 15.06 g of crude 1-acetyl-3-(1-hydroxyethyl) bicyclo [1.1.1]pentane in the form of a yellowish oil (about 80% pure by GC): $^1$H NMR delta 1.05 (d, J-6.4 Hz, 3H), 1.81 (d, J-9.0 Hz, 3H), 1.87 (d, J-9.0 Hz, 3H), 2.06 (s, 3H), 3.74 (g, J-6.4 Hz, 1H); $^{13}$C NMR (major peaks) 19.17, 25.95, 42.70, 43.41, 48.49, 66.21, 206.90; GC-MS, m/z (relative intensity) 139(24, M-Me), 121(63), 111(27), 95(30), 93(68), 91(59), 77(81), 71(100).

An attempt at purification by short-path distillation (100°–115° C./0.4 mm Hg) led to partial decomposition. Crude 1-acetyl-3-(1-hydroxyethyl)bicyclo[1.1.1]pentane (7.5 g) diluted with 25 ml of dioxane was slowly added to a vigorously stirred solution of sodium hypobromite prepared by slow addition of 18.5 ml (0.36 mol) of bromine to a well stirred solution of 40.0 g (1.0 mol) of sodium hydroxide in 300 ml of water. Temperature during preparation of the hypobromite as well as the addition of 3 was maintained below 5° C. The reaction mixture was stirred for 1 h at ice bath temperature, then 3 h at room temperature and finally 1 h at 50° C. Excess hypobromite was destroyed by addition of 5 g of sodium bisulfite, the mixture was extracted with 3×50 ml of chloroform, acidified with 55 ml of conc. HCl and the product was extracted with ether for 10 hr. Ether was evaporated, the residue was dried under reduced pressure and the crude diacid (7b) was washed with 10 ml of boiling chloroform. Filtering off the cold suspension gave 2.76 g (35% yield) of the product.

Example 29

1,3-Bis(chlorocarbonyl)bicyclo[1.1.1]pentane 24.6 g (0.157 mol) of the diacid (7b) and 45 ml of thionyl chloride were refluxed until a clear solution was formed (about 10 h). Excess thionyl chloride was evaporated and the crystalline residue was distilled on a Kugel-Rohr (120° C./12 mm Hg) giving 26.92 g (89% yield) of product: mp 55°–57° C.; $^1$H NMR delta 2.58 (s); $^{13}$C NMR delta 44.57, 54.80, 169.55; IR (C—O) 1794; MS, m/z (relative intensity) 159(1.4, M-Cl), 157(4.4, M-Cl), 131(1.3), 129(4.0), 103(11.6), 101(32.4), 65(100); HRMS, m/z (calcd for C$_7$H$_6$ClO$_2$: 157.0056) 157.0054. Anal. Calcd for C$_7$H$_6$Cl$_2$O$_2$: C, 43.55; H, 3.13; Cl, 36.74; Found: C, 43.48; H, 3.14; Cl, 36.76.

Example 30

Dimethyl bicyclo[1.1.1]pentane-1,3-dicarboxylate 26.92 g (0.139 mol) of the product in Example 29 was slowly added to 75 ml of stirred anhydrous methanol. When the addition was completed the mixture was refluxed for 30 min. Evaporation of methanol gave a crystalline solid which after short-path distillation (125°–130° C./12 mm Hg) gave 25.24 g (99% yield) of product: mp 92° C.; $^1$H NMR delta 2.30 (s, 6), 3.67 (s, 6H); $^{13}$C NMR delta 37.46, 51.45, 52.68, 169.31; IR: 1739, 1211; MS, m/z (relative intensity) 153(31, M-OMe), 152(57), 125(51), 124(80), 96(100), 66(70), 64(59); HRMS, m/z (calcd for C$_8$H$_9$O$_3$: 153.0549; Anal. Calcd for C$_9$H$_{12}$O$_4$: C, 58.69; H, 6.57; Found: C, 58.78; H, 6.58.

Example 31

3-Methoxycarbonylbicyclo[1.1.1]pentane-1-carboxylic acid

To a gently refluxed and stirred solution of 25.24 g (0.137 mol) of the dimethyl ester product of Example 30 in 200 ml of methanol, a solution of 5.50 g (0.137 mol) of sodium hydroxide in 50 ml of methanol was added during 1.5 hr. When the addition was completed the mixture was stirred and refluxed for 1 h. Methanol was evaporated and the white sodium salts were vacuum dried. The salts were dissolved in 150 ml of water, unreacted Example 30 product was extracted with 4×50 ml of methylene chloride (3.00 g of Example 30 product was recovered) and the aqueous phase was acidified with 12 ml of concentrated hydrochloric acid. The product was extracted with 4×50 ml of methylene chloride, and the extracts were dried with sodium sulfate. Evaporation of the solvent gave 18.12 g (88% yield corrected for recovered Example 30 product) of crude product (mp 137.5°–140° C.). Crystalization from heptane-chloroform gave pure product: mp 139.5°–140° C. (lit.[1] mp 139.5°–140.2° C.); $^1$H NMR delta 2.35 (s, 6H0, 3.69 (s, 3H); $^{13}$C NMR delta 37.43, 51.80, 52.69, 169.61, 174.73; MS, m/z (relative intensity) 153(1, M-OH), 152(4), 139(13), 138(14), 125(10), 124(16), 111(17), 110(31), 96(53), 93(22), 83(29), 82(100), 87(52), 86(62), 65(98).

2. Liquid Crystals

Certain disubstituted oligomers (2) of [1.1.1]propellane exhibit mesogenic behavior, for example, (2a,n=3) and (2g,n=3). (2a,n=3) has been found to have the following characteristics: K 136 S$_G$166N 194 I, while (2g,n=3) has the following: K 55 S$_B$ 95 I.

These compounds are representative of a potentially large class of liquid crystals which promise unique and useful physical properties. Crystallographic data show the length of the rigid core of (2a,n=3) to be around 8.55 A, comparable to biphenyl, with a value of 2.49 A for the diameter of a cylinder on which the carbon atoms are located.

A related liquid crystal provided by the present invention has the following formula:

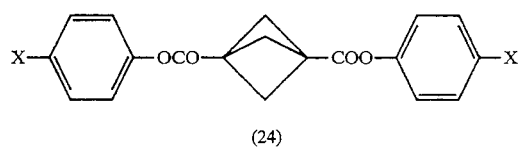

(24)

(a) X = OMe  K 143 N 145.5 I
(b) X = OBu  K 129 N 144 I

These compounds may be created by linking together various liquid crystal building blocks or precursors. Examples of such building blocks are the following:

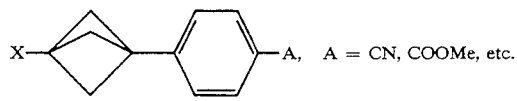

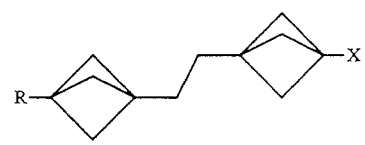

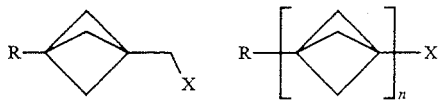

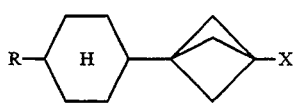

where X=COOH or OH.

Example 32

Preparation of Liquid Crystal Building Blocks

Exemplary preparations of liquid crystal building blocks in accordance with the present invention are shown below.

(1) $\xrightarrow{(AcS)_2}$ (2r) $\xrightarrow{OH^-, H^+}$ (2s)   (BB)

RI + (1) $\longrightarrow$ (7e) $\xrightarrow{Bu_3SnH, biacetyl}$ (7f)   (CC)

Where R is, for example, an alkyl, a cycloalkyl (e.g.

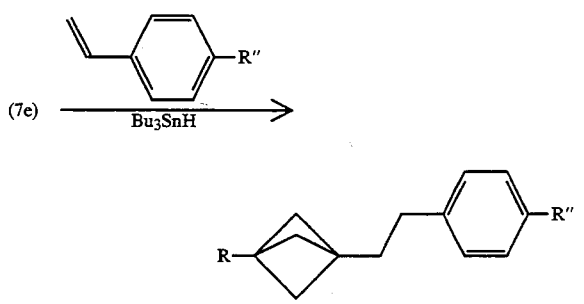

an aryl (e.g.

or an iodine substituted alkyl, cycloalkyl or aryl.

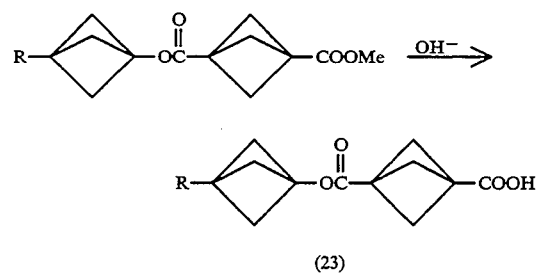

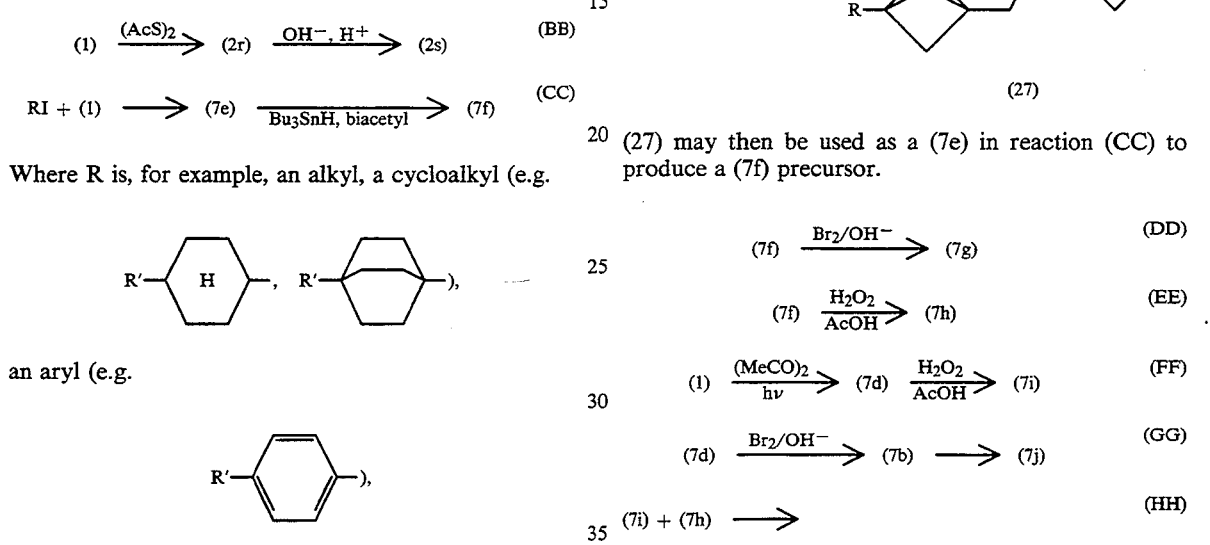

(27) may then be used as a (7e) in reaction (CC) to produce a (7f) precursor.

(7f) $\xrightarrow{Br_2/OH^-}$ (7g)   (DD)

(7f) $\xrightarrow{H_2O_2}{AcOH}$ (7h)   (EE)

(1) $\xrightarrow{(MeCO)_2}{h\nu}$ (7d) $\xrightarrow{H_2O_2}{AcOH}$ (7i)   (FF)

(7d) $\xrightarrow{Br_2/OH^-}$ (7b) $\longrightarrow$ (7j)   (GG)

(7i) + (7h) $\longrightarrow$   (HH)

Example 33

Preparation of Liquid Crystals

Exemplary preparations of liquid crystals in accordance with the present invention are shown below.

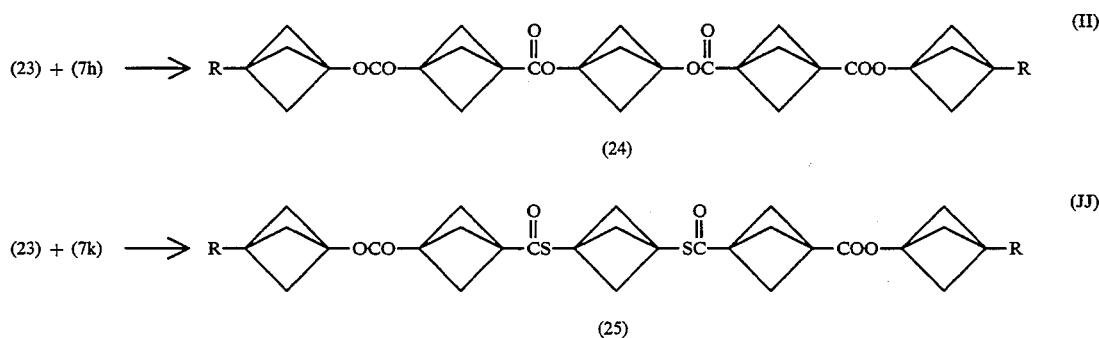

(23) may also be reacted with 1,4-cyclohexanol or 1,4-butanol to produce corresponding liquid crystals.

Preferably, R does not have an amine, sulfur, or hydroxyl group, since the presence of such a group generally makes the intermediate compound (7e) unstable.

Example 34

Exemplary Liquid Crystals

Exemplary liquid crystals provided by the present invention are shown in the following chart.

$$A-[\text{ring}]_m-X-[\text{ring}(Z,Z)]_n-Y-[\text{ring}]_p-B \quad (6)$$

| | A | m | X | n | Y | p | B | Z |
|---|---|---|---|---|---|---|---|---|
| (a) | CH$_3$CO | 0 | S | 3 | S | 0 | COCH$_3$ | H |
| (b) | MeO–⌬– | 0 | OC | 1–3 | CO | 0 | –⌬–OMe | H, F, Cl, CN |
| (c) | C$_5$H$_{11}$ | 1 | OOC | 1–3 | COO | 0 | –⌬–CN | H |
| (d) | C$_5$H$_{11}$ | 1 | CH$_2$CH$_2$ | 1 | COO | 0 | –⌬–CN | H |
| (e) | C$_5$H$_{11}$ | 1 | CH$_2$CH$_2$ | 1 | COO | 1 | –⌬–CN | H |
| (f) | C$_5$H$_{11}$O | 2 | COO | 2 | OOC | 2 | OC$_5$H$_{11}$ | H |
| (g) | C$_5$H$_{11}$–⬡(H)– | 1 | COO | 1 | OOC | 1 | –⬡(H)–C$_5$H$_{11}$ | H |
| (h) | C$_5$H$_{11}$–⬡(H)– | 1 | OOC | 1 | COO | 1 | –⬡(H)–C$_5$H$_{11}$ | H, Cl, F, CN |
| (i) | C$_5$H$_{11}$–⬡(H)– | 1 | COO(CH$_2$)$_{1-3}$ | 0 | (CH$_2$)$_{1-3}$OCO | 1 | –⬡(H)–C$_5$H$_{11}$ | |
| (j) | C$_5$H$_{11}$ | 1 | OOC–⬡(H)– | 0 | COO | 1 | C$_5$H$_{11}$ | |
| (k) | C$_5$H$_{11}$ | 1 | OOC | 1 | COO | 0 | –⌬–CN | H |
| (l) | C$_5$H$_{11}$–bicyclic– | 1 | OOC | 2 | COO | 1 | –bicyclic–C$_5$H$_{11}$ | H |

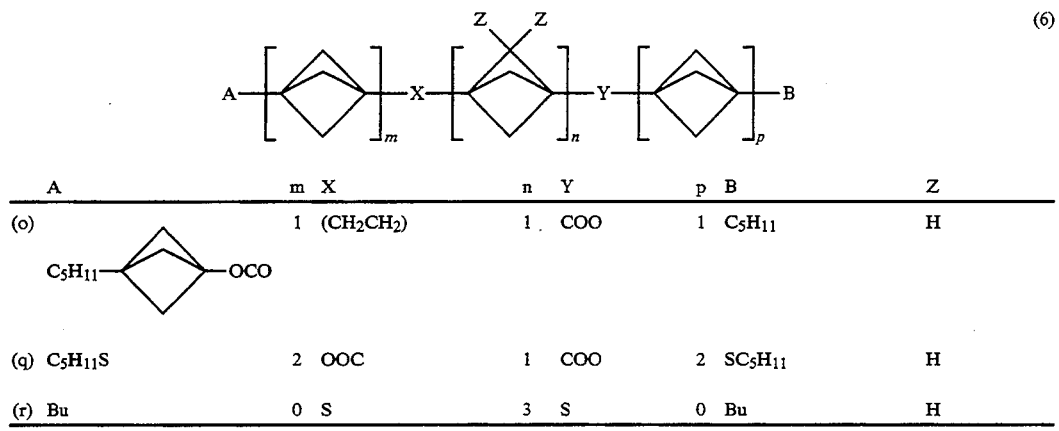

| A | m | X | n | Y | p | B | Z |
|---|---|---|---|---|---|---|---|
| (o) C₅H₁₁–◇–OCO | 1 | (CH₂CH₂) | 1 | COO | 1 | C₅H₁₁ | H |
| (q) C₅H₁₁S | 2 | OOC | 1 | COO | 2 | SC₅H₁₁ | H |
| (r) Bu | 0 | S | 3 | S | 0 | Bu | H |

3. Surfactants

Figure 14:
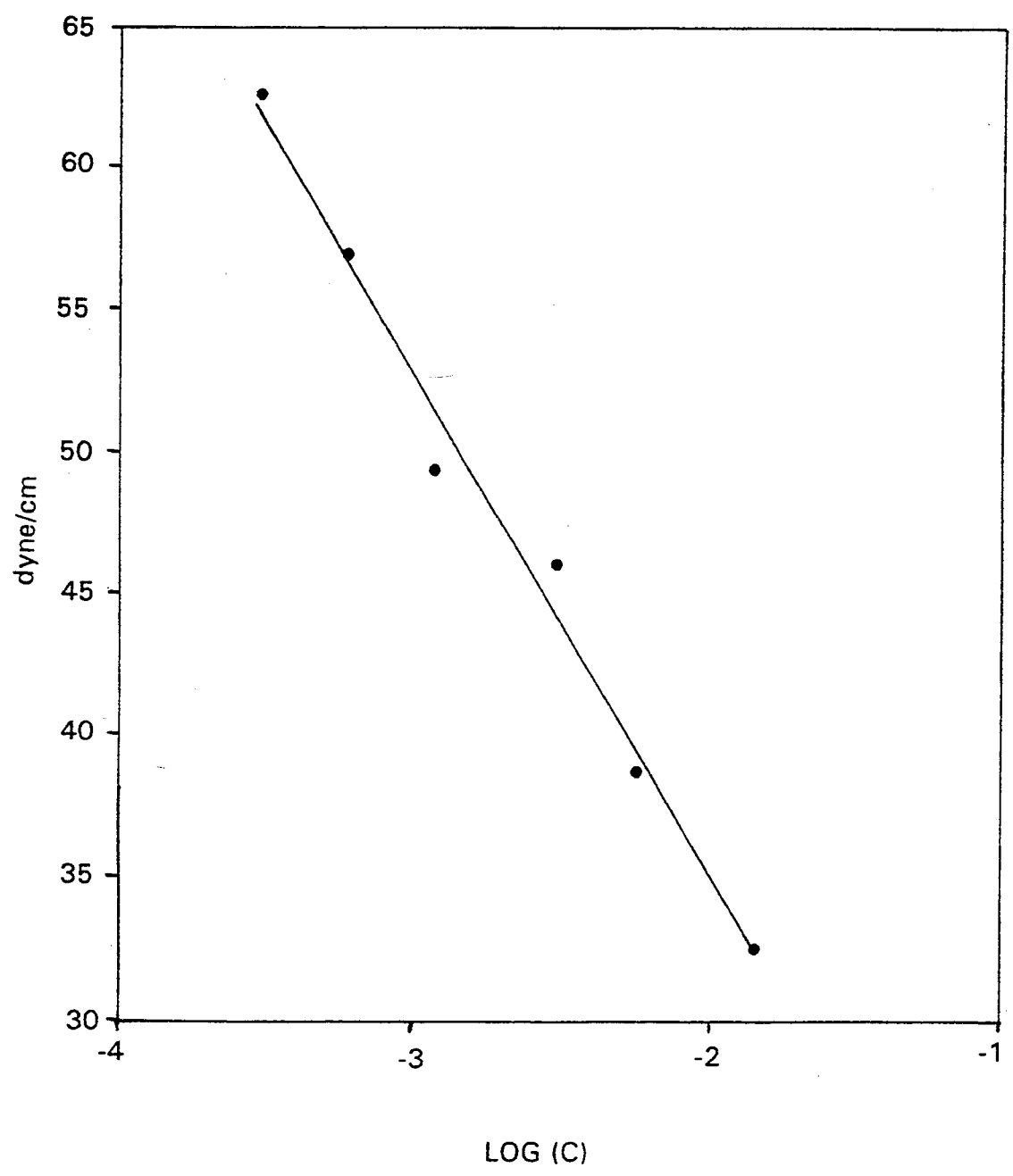
FIG. 14 is a graph illustrating the surface activity of a poly[1.1.1]propellane telomer having three bicyclo ring units and —$CO_2K$ as the surface active end group.

Surface activity data for (26) is shown in FIG. 14.

(26)

The graph shows experimental data found on such compound, plotting the log of the concentration against surface tension (dyne/cm). A line fit through the data points has slope −17.67 and intercept −0.2291.

The instant invention has been disclosed in connection with specific embodiments. However, it will be apparent to those skilled in the art that variations from the illustrated embodiments may be undertaken without departing the sprirt and scope of the invention.

What is claimed is:

1. A poly[1.1.1]propellane having the formula:

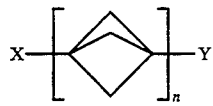

where n, the chain length, is greater than or equal to 2, and X and Y are either H or a linking group wherein at least one of X or Y is a linking group.

2. A poly[1.1.1]propellane having the formula:

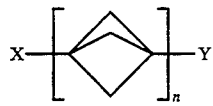

where n, the chain length, is greater than or equal to 2, and wherein X and Y are selected from:
a hydrogen;
a group including a carbon atom wherein the carbon atom is bonded to a propellane bridgehead carbon;
a group including a heteroatom wherein the heteroatom is bonded to a propellane bridge carbon;
a group which is polymerizable;
a nucleophilic group;
a electrophilic group; or
a charged group.

3. The poly[1.1.1]propellane of claim 2 where X and Y are groups selected from:
a hydrogen;
a group which is polymerizable;
a nucleophilic group;
a electrophilic group; or
a charged group.

4. The poly [1.1.1]propellane of claim 3 where X and Y are groups selected from a hydrogen or a nucleophilic group.

5. The poly[1.1.1]propellane of claim 2 wherein n is 20 or less.

6. The poly[1.1.1]propellane of claim 2 wherein X and Y are groups selected from:
a hydrogen;
a CN, NC, C(CH₂O)₃P, C(CH₂CH₂)₃N, CH(COCH₃)₂, COOH, CSSH, or C(CH₂SH)₃ group;
a SR, PR₂, NR₂, BR₂ or SiR₂Cl group where R is selected from hydrogen, alkyls and aryls;
a methyl or substituted methyl, 1,4-phenylene, 1,3-phenylene, trans-ethylene, cis-ethylene, or quinone group;
an alkene or substituted alkene group;
a CH₂NRR' or CH₂Li group where R and R' is selected from hydrogen, alkyls and aryls;
a C(CH₂O)₃SiCl, SO₂Cl, CH₂Br or COCl group;
an SO₃ or NR₃⁺ group where R is selected from hydrogen, alkyls and aryls;
an alkyne; or
a CH(CO₂Et)₂, C(CO₂Et)₃, COOMe, CH₂OH, SCOMe, CH₂OCOCMe=CH₂ or CH(COOC₁₆H₃₃)₂ group.

7. The poly[1.1.1]propellane of claim 2 wherein X and Y are selected such that:
both X and Y are SCOMe; both X and Y are COOR where R is an alkyl or aryl group; both X and Y are COOH; both X and y are Br; both X and y are SButyl; both X and Y are SH; X is phenylCH₂ and Y is Br; or X is H and Y is CooR where R is an alkyl or aryl group.

8. The poly[1.1.1]propellane of claim 2 wherein X and Y are selected from hydrogen, COOH, and COOR where R is an alkyl or aryl group.

9. The poly[1.1.1]propellane of claim 2 wherein n is 2, 3, 4, or 5.

10. The poly[1.1.1]propellane of claim 2 wherein n is 6, 7, 8, 9, or 10.

11. The poly[1.1.1]propellane of claim 2 wherein n is greater than 10.

12. The poly[1.1.1]propellane of claim 2 wherein a bridge carbon of said propellane is substituted with chlorine or fluorine.

13. The poly[1.1.1]propellane of claim 2 wherein X and Y are groups selected from OH or SH.

14. A molecular building beam comprising a poly[1.1.1]propellane of claim 2.

15. A molecular structure comprising a building beam of claim 14.

16. A molecular structure comprising a plurality of building beams of claim 2 and a plurality of connecting units each having a plurality of accepting sites wherein each of said building beams is connected to an accepting site of a connecting unit by means of either said X or Y group.

17. The molecular structure of claim 16 wherein said connecting units having accepting sites are metal compounds.

18. The molecular structure of claim 16 wherein said connecting units having accepting sites comprise a supporting surface wherein a plurality of building beams are anchored to said supporting surface.

19. The molecular structure of claim 16 which comprises a layer of building beams anchored to a surface wherein said surface functions as a connecting unit with accepting sites to anchor said building beams.

20. The molecular structure of claim 19 wherein said surface is a flat surface and wherein said building beams are anchored to metal atoms on said surface.

21. The molecular structure of claim 20 wherein the X and Y groups of said building beam are selected from hydrogen, COOH and COOR where R is an alkyl or aryl group.

22. The molecular structure of claim 21 wherein the said building beam n is 2, 3, 4, or 5.

23. The molecular structure of claim 16 wherein said connecting units having accepting sites are aromatic groups.

24. The molecular structure of claim 16 wherein said connecting units are boranes.

25. The molecular structure of claim 16 wherein said connecting units are metal complexes of $C_5H_5$.

26. The molecular structure of claim 16 wherein said connecting units having accepting sites are nucleophiles and X is an electrophilic group.

27. The molecular structure of claim 16 wherein said connecting units having accepting sites are electrophiles and X is a nucleophilic group.

28. The molecular structure of claim 16 which comprises a whip, comb, scaffolding or net structure.

29. The molecular structure of claim 16 wherein each connecting unit includes two accepting sites.

30. The molecular structure of claim 16 wherein each connecting unit includes at least three accepting sites.

31. The molecular structure of claim 16 wherein the connecting units are selected from a precursor; the precursor being selected from $BX_3$, $SiX_4$, and $PX_3$, where X is selected from Cl, Br and I.

32. The molecular structure of claim 16 wherein the connecting units are provided on a solid surface.

33. The molecular structure of claim 16 wherein connecting units are provided as metal atoms on a solid surface.

34. A molecular building beam comprising a plurality of staffs each of which is a single bicyclo[1.1.1]pentane ring or a plurality of directly linked bicyclo[1.1.1]pentane rings each staff being connected to at least one other staff by a connecting fragment.

35. The molecular building beam of claim 34 wherein said connecting fragment is an alkyne.

36. The molecular building beam of claim 34 wherein said connecting fragment is a group containing a metal having magnetic properties.

37. The molecular building beam of claim 34 wherein said connecting fragment is a group having conducting properties.

38. The molecular building beam of claim 34 wherein said connecting fragment is a group having magnetic properties.

39. The molecular building beam of claim 34 wherein said connecting fragment is an alkene.

* * * * *